(12) United States Patent
Song et al.

(10) Patent No.: US 10,248,779 B2
(45) Date of Patent: Apr. 2, 2019

(54) MOBILE TERMINAL, SMART WATCH, AND METHOD OF PERFORMING AUTHENTICATION WITH THE MOBILE TERMINAL AND THE SMART WATCH

(71) Applicant: LG ELECTRONICS INC., Seoul (KR)

(72) Inventors: Yoomee Song, Seoul (KR); Miyoung Kim, Seoul (KR); Jiyoun Lee, Seoul (KR); Younghoon Song, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 25 days.

(21) Appl. No.: 14/903,046

(22) PCT Filed: Jul. 22, 2014

(86) PCT No.: PCT/KR2014/006664
§ 371 (c)(1),
(2) Date: Jan. 5, 2016

(87) PCT Pub. No.: WO2015/016524
PCT Pub. Date: Feb. 5, 2015

(65) Prior Publication Data
US 2017/0235935 A1 Aug. 17, 2017

(30) Foreign Application Priority Data
Jul. 30, 2013 (KR) .................. 10-2013-0090453

(51) Int. Cl.
*G06F 21/00* (2013.01)
*G06F 21/35* (2013.01)
*G06F 21/32* (2013.01)
(Continued)

(52) U.S. Cl.
CPC ............ *G06F 21/35* (2013.01); *A61B 5/0022* (2013.01); *A61B 5/0093* (2013.01);
(Continued)

(58) Field of Classification Search
CPC .......... G06F 21/32; G06F 21/33; G06F 21/35; G06F 3/0488; G06F 19/00; G06F 3/017;
(Continued)

(56) References Cited

U.S. PATENT DOCUMENTS 8,166,523 B2 * 4/2012 Ezaki ..................... G06F 21/32
380/247
2005/0221798 A1 * 10/2005 Sengupta ................ H04M 1/67
455/411

(Continued)

FOREIGN PATENT DOCUMENTS

CN 1672357 A 9/2005
JP 2009-2111 A 1/2008
(Continued)

*Primary Examiner* — Joseph P Hirl
*Assistant Examiner* — Chi D Nguy
(74) *Attorney, Agent, or Firm* — Birch, Stewart, Kolasch & Birch, LLP

(57) ABSTRACT

The present invention relates to a mobile terminal and a method capable of performing authentication using a smart watch, including: detecting a request for authentication for executing an application; measuring a user's heartbeat rhythm through a sensor mounted in a bottom of the smart watch when detecting the request for the authentication; and comparing the measured heartbeat rhythm with an already-stored heartbeat rhythm and thus performing the authentication on the application.

11 Claims, 19 Drawing Sheets

(51) Int. Cl.
*G06F 3/0488* (2013.01)
*G06F 21/33* (2013.01)
*G06Q 20/32* (2012.01)
*A61B 5/00* (2006.01)
*A61B 5/024* (2006.01)
*A61B 5/1172* (2016.01)
*G06F 1/16* (2006.01)
*G06F 3/01* (2006.01)
*G06F 19/00* (2018.01)
*A61B 5/026* (2006.01)

(52) U.S. Cl.
CPC ........ *A61B 5/02416* (2013.01); *A61B 5/1172* (2013.01); *A61B 5/681* (2013.01); *A61B 5/743* (2013.01); *A61B 5/7475* (2013.01); *G06F 1/163* (2013.01); *G06F 3/017* (2013.01); *G06F 3/0488* (2013.01); *G06F 19/00* (2013.01); *G06F 21/32* (2013.01); *G06F 21/33* (2013.01); *G06Q 20/3223* (2013.01); *A61B 5/0077* (2013.01); *A61B 5/0261* (2013.01); *A61B 5/7203* (2013.01); *A61B 2562/0247* (2013.01); *A61B 2562/0257* (2013.01)

(58) Field of Classification Search
CPC ............ G06Q 20/3223; H04L 63/0853; H04L 63/0861; A61B 5/681; A61B 5/1172; A61B 5/02416
See application file for complete search history.

(56) References Cited

U.S. PATENT DOCUMENTS

| | | | | |
|---|---|---|---|---|
| 2006/0288233 | A1* | 12/2006 | Kozlay | G06F 21/32 713/186 |
| 2010/0113950 | A1* | 5/2010 | Lin | A61B 5/02438 600/509 |
| 2010/0245131 | A1* | 9/2010 | Graumann | G01P 15/00 341/20 |
| 2010/0263031 | A1* | 10/2010 | Tsuchiya | G06F 21/32 726/7 |
| 2012/0068820 | A1 | 3/2012 | Mollicone et al. | |
| 2012/0229411 | A1* | 9/2012 | Arai | G06F 3/0488 345/173 |
| 2014/0196131 | A1* | 7/2014 | Lee | G06F 21/32 726/7 |
| 2014/0208258 | A1* | 7/2014 | Yuen | G06F 3/0236 715/780 |
| 2016/0188181 | A1* | 6/2016 | Smith | G06F 3/048 715/765 |

FOREIGN PATENT DOCUMENTS

| | | |
|---|---|---|
| JP | 2008-73461 A | 4/2008 |
| KR | 10-2012-0098538 A | 9/2012 |
| WO | WO 2004/012388 A1 | 2/2004 |
| WO | WO 2012/102111 A1 | 8/2012 |

* cited by examiner

[Fig. 1]
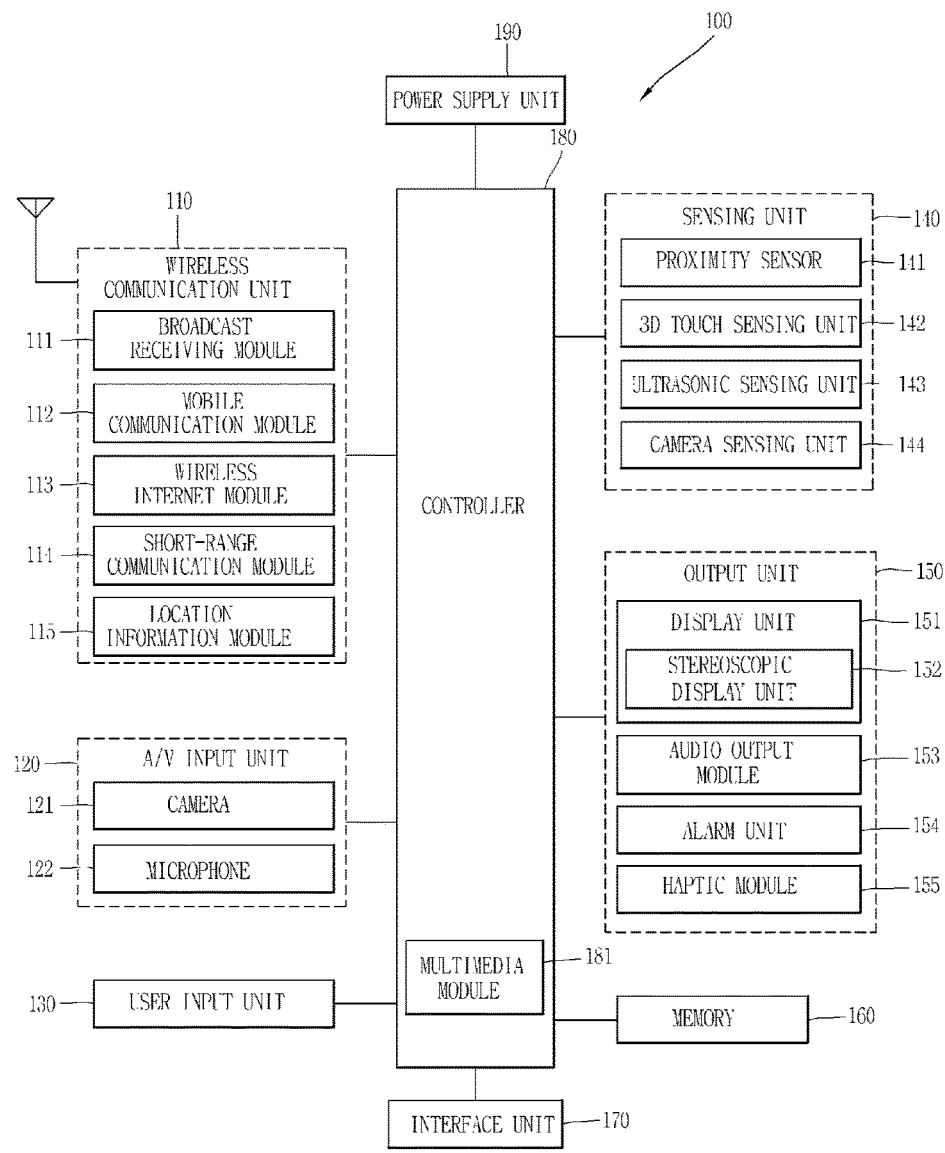

[Fig. 2a]
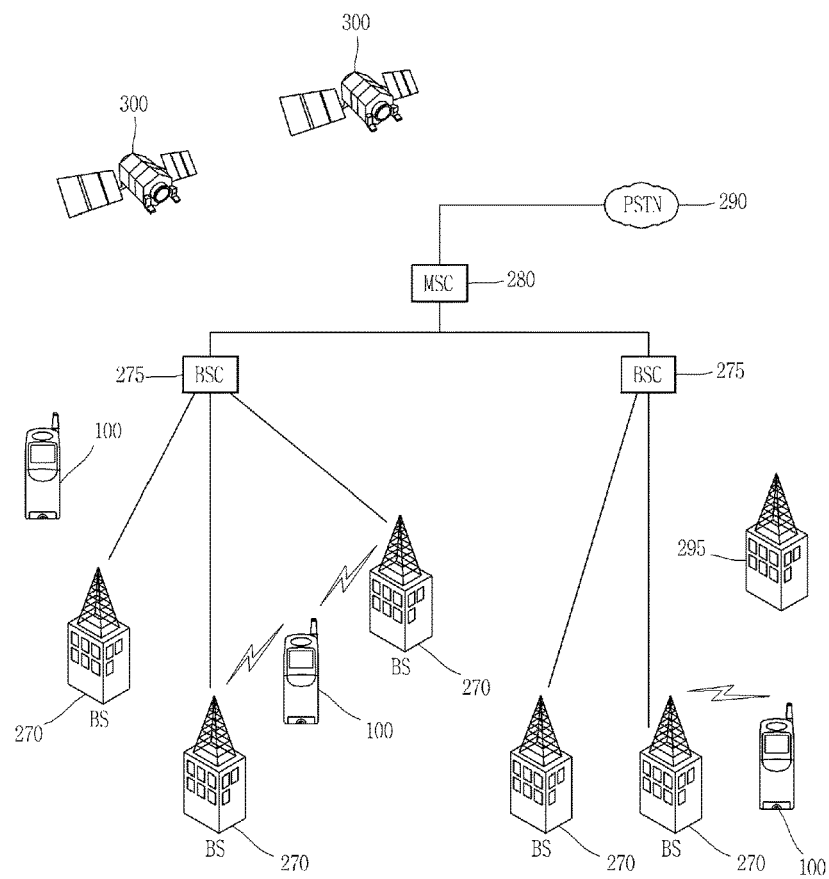
[Fig. 2b]
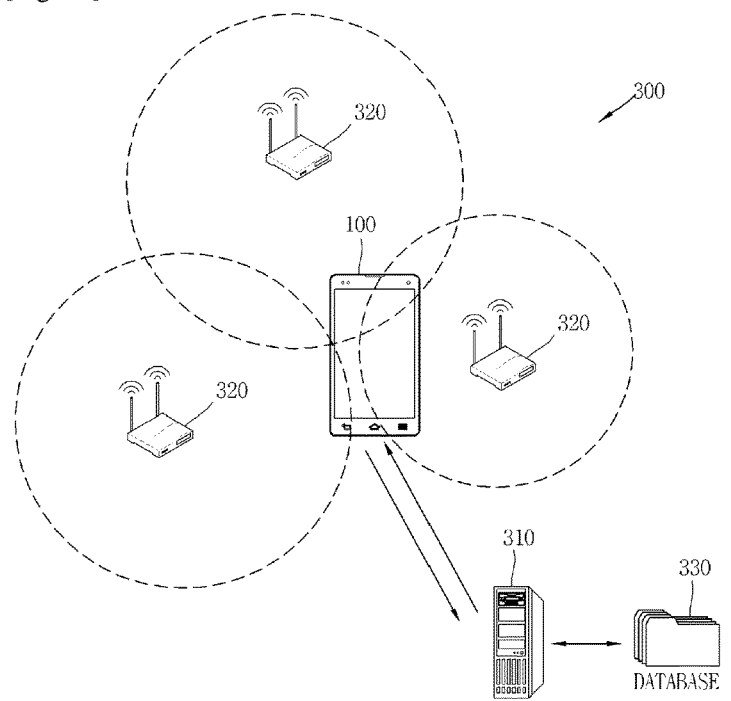

[Fig. 3]
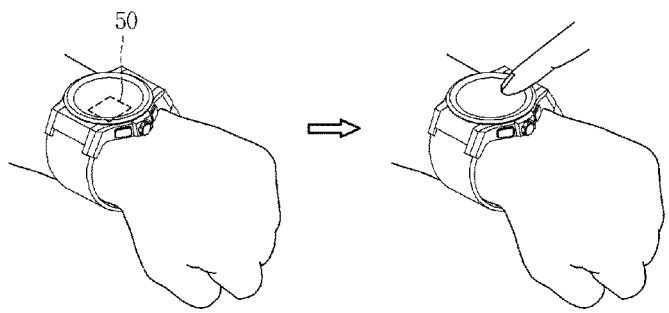
[Fig. 4a]
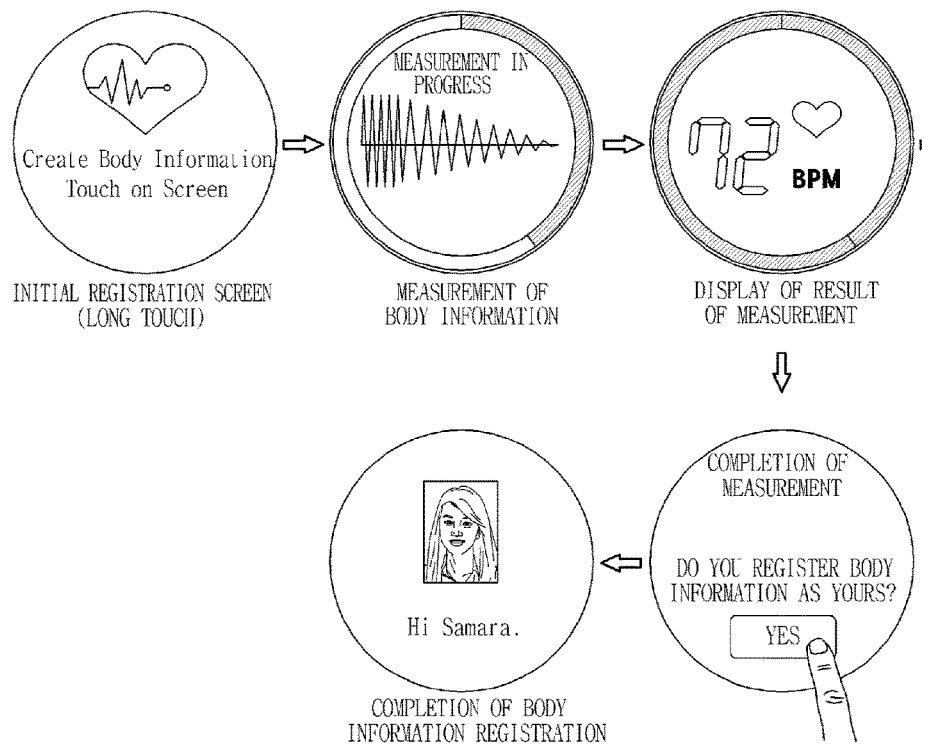

[Fig. 4b]
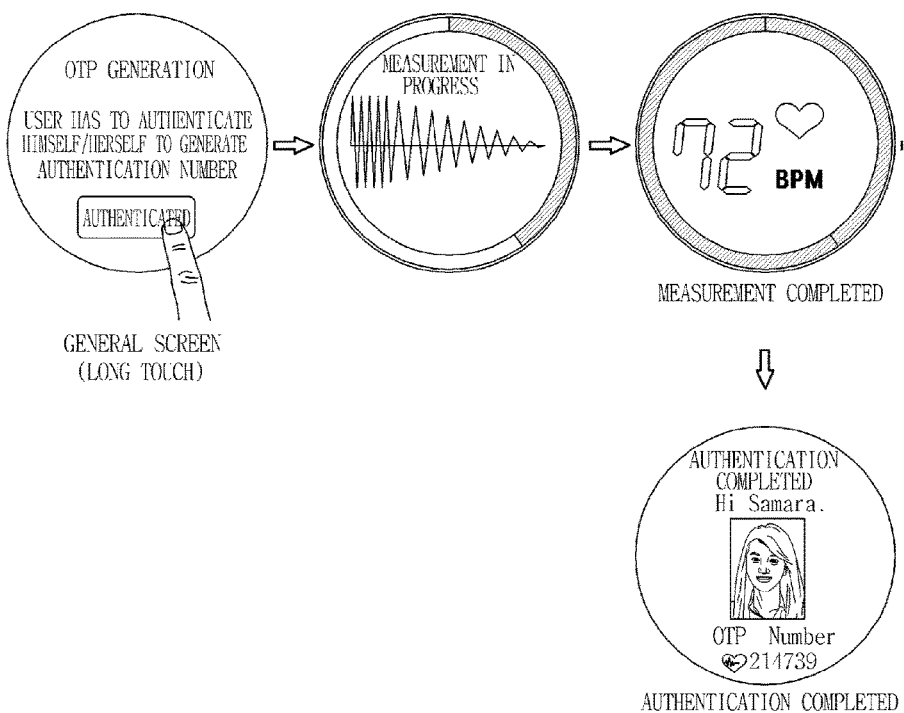
[Fig. 5]
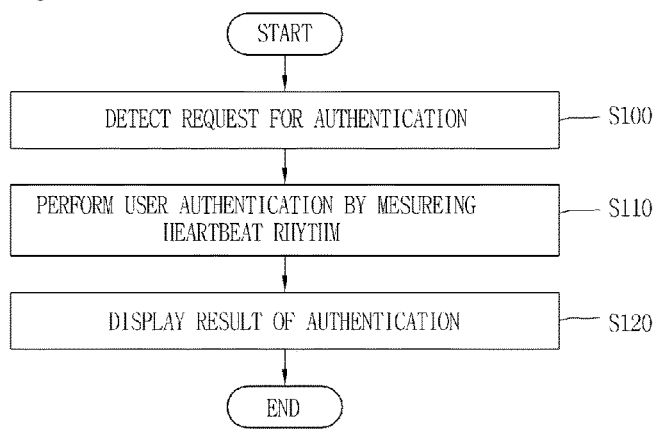

[Fig. 6a]
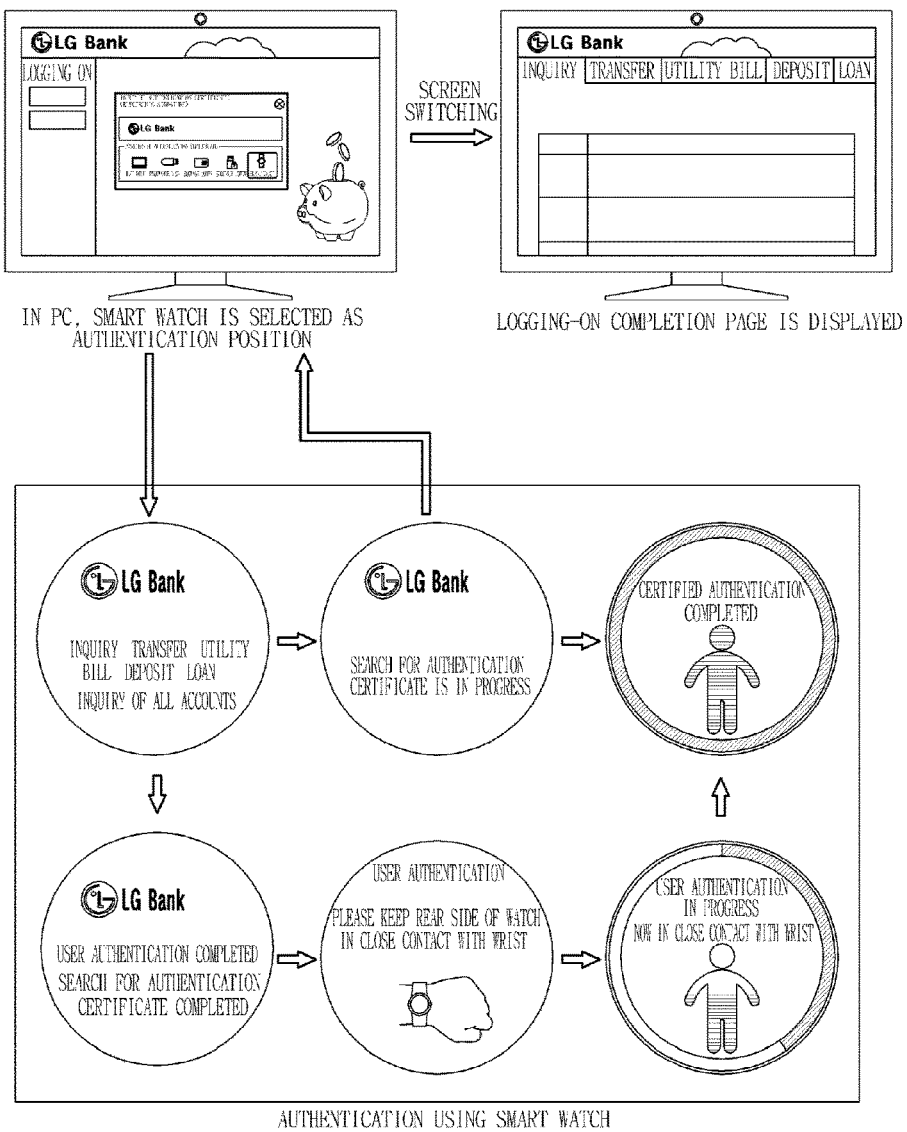
[Fig. 6b]
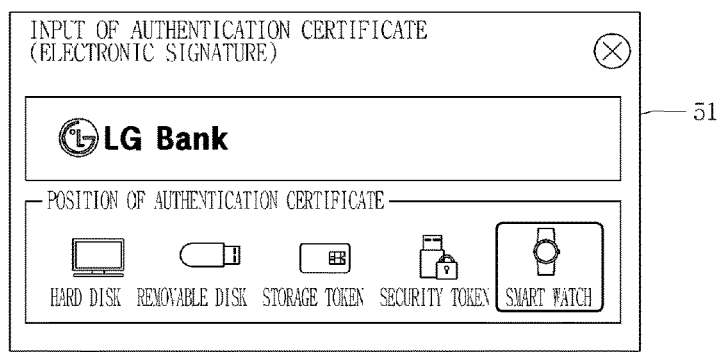

[Fig. 7]
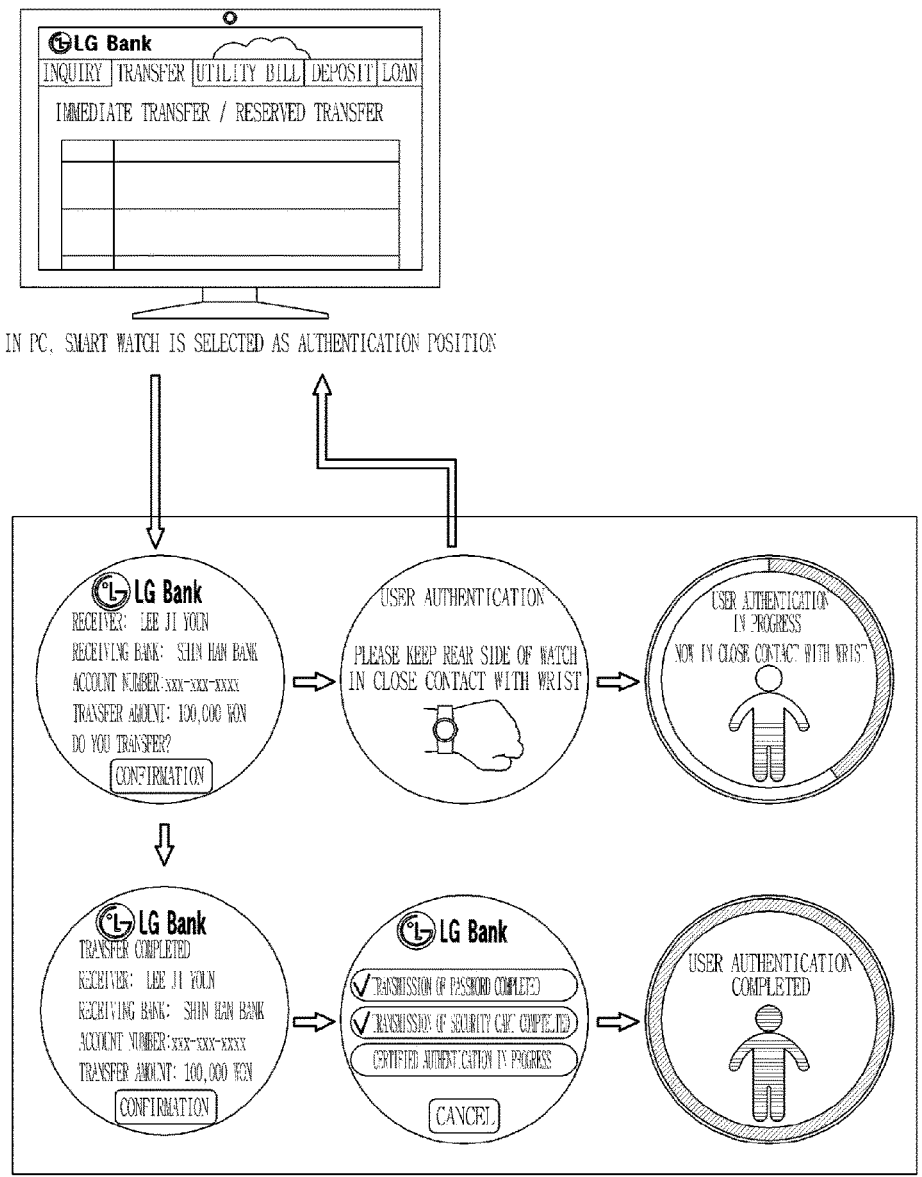

[Fig. 8]
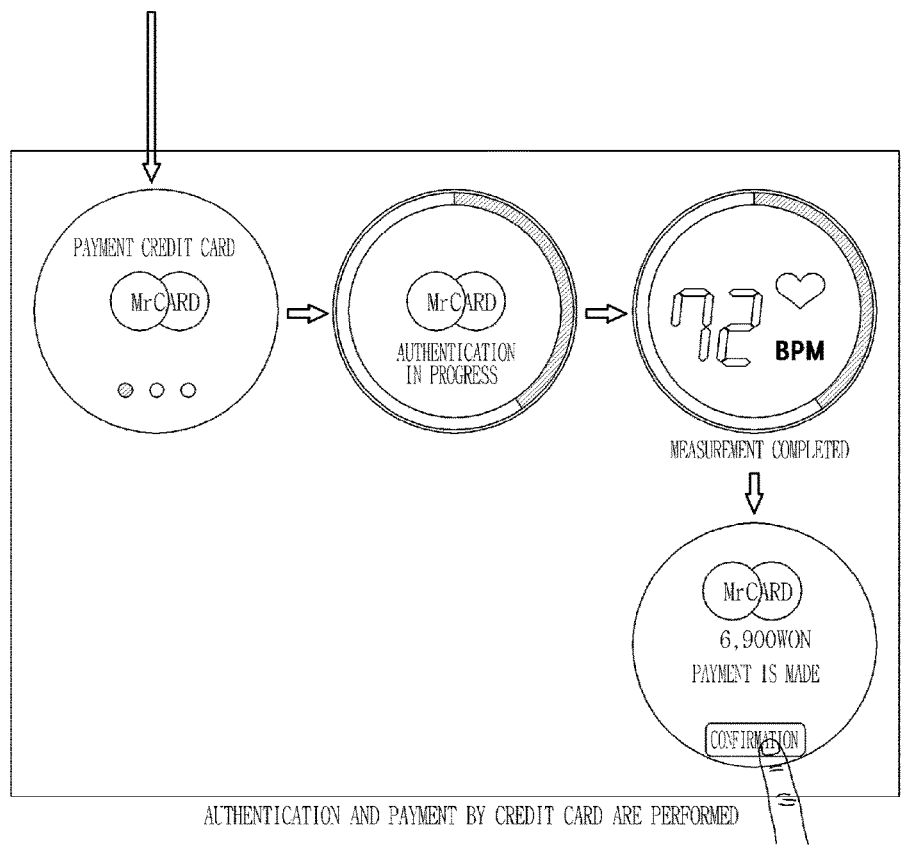

[Fig. 9a]
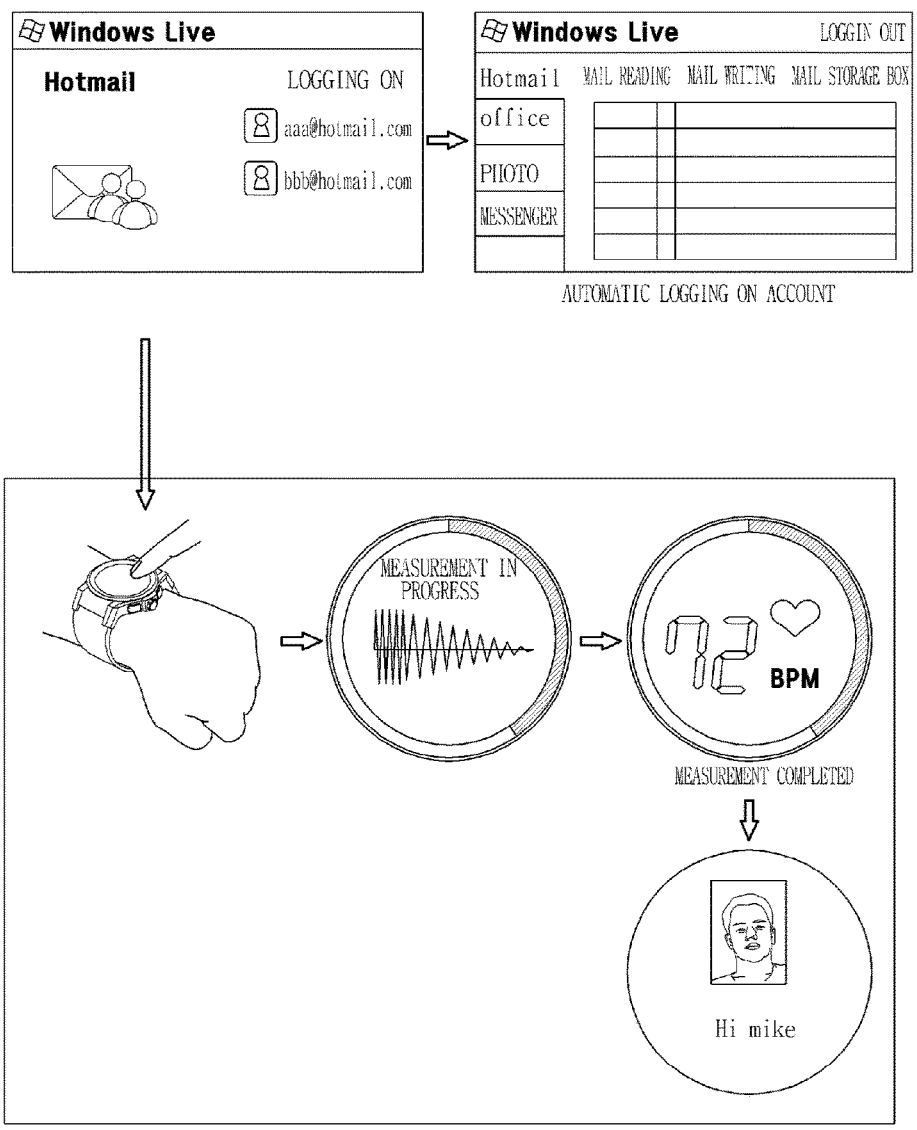

[Fig. 9b]
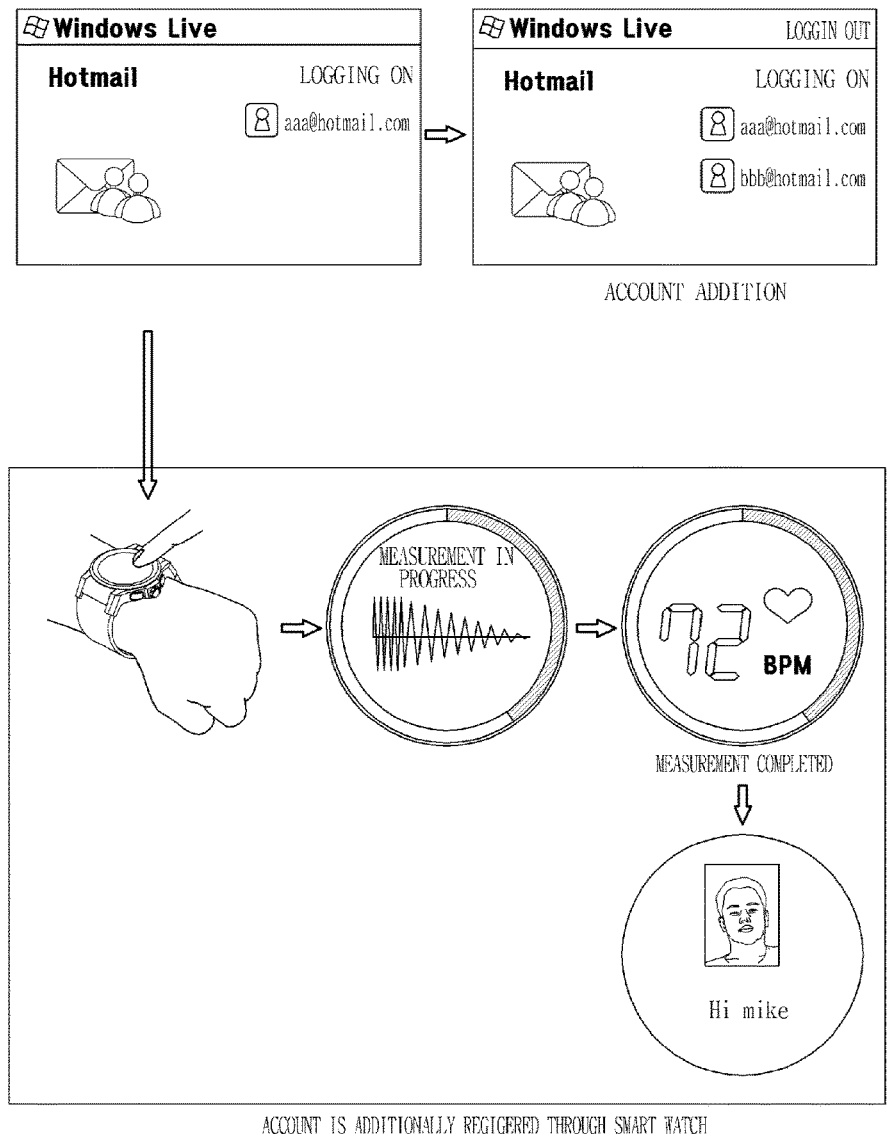
ACCOUNT IS ADDITIONALLY REGISTERED THROUGH SMART WATCH
[Fig. 10a]
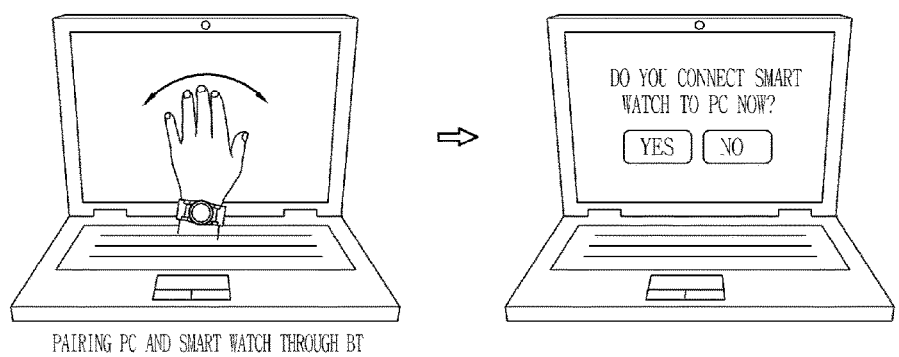
PAIRING PC AND SMART WATCH THROUGH BT

[Fig. 10b]
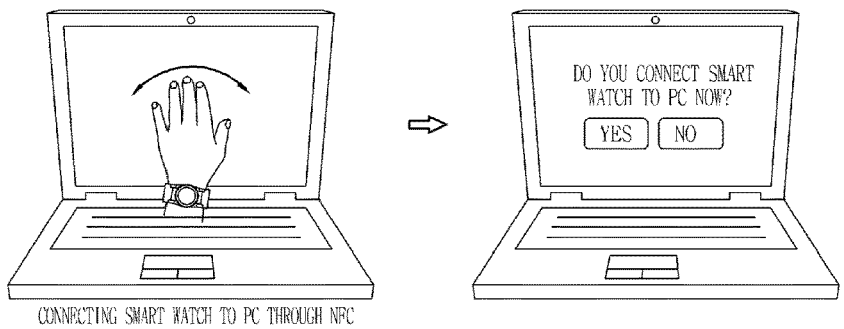
[Fig. 11]
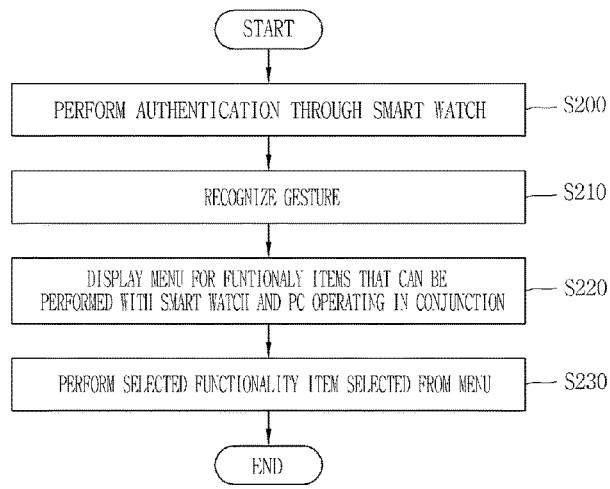
[Fig. 12]
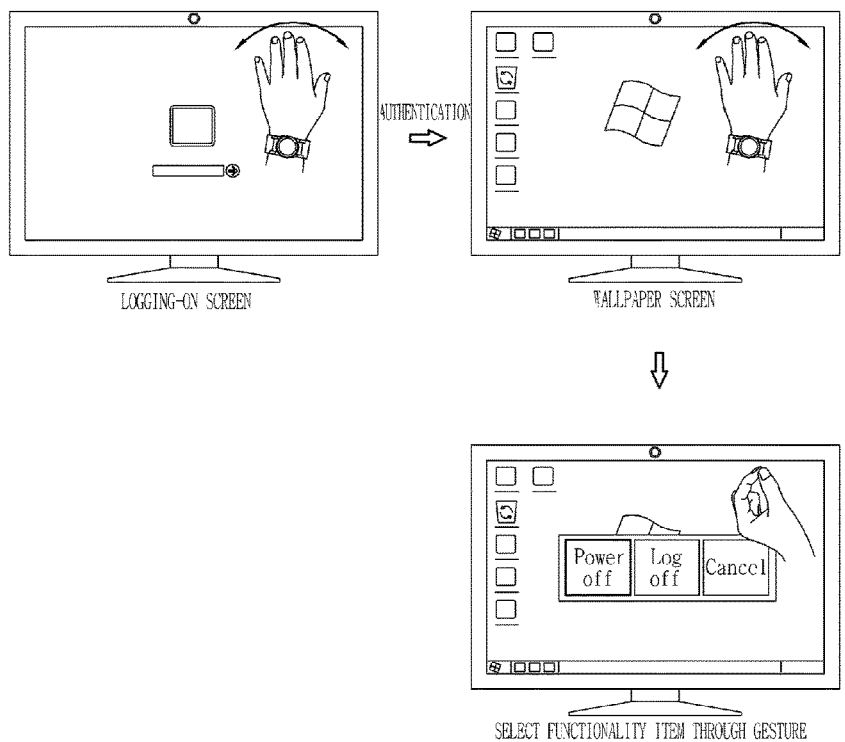

[Fig. 13]
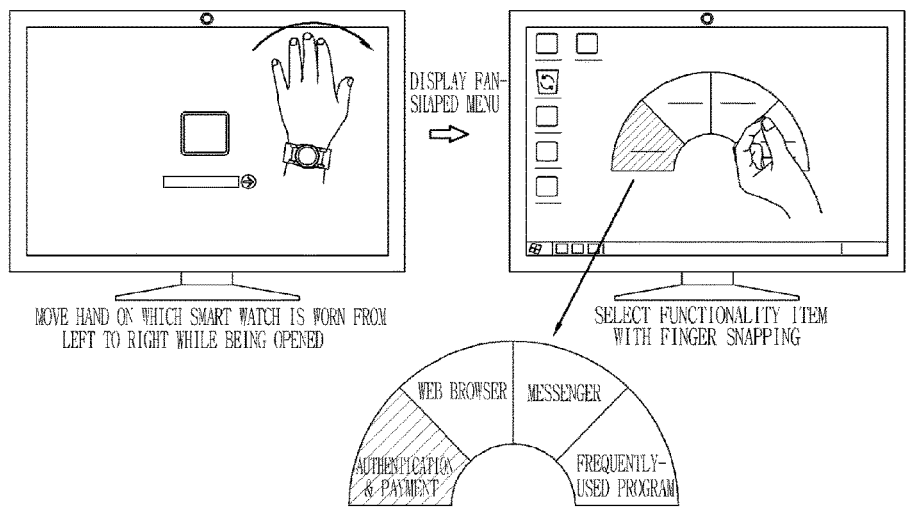
[Fig. 14a]
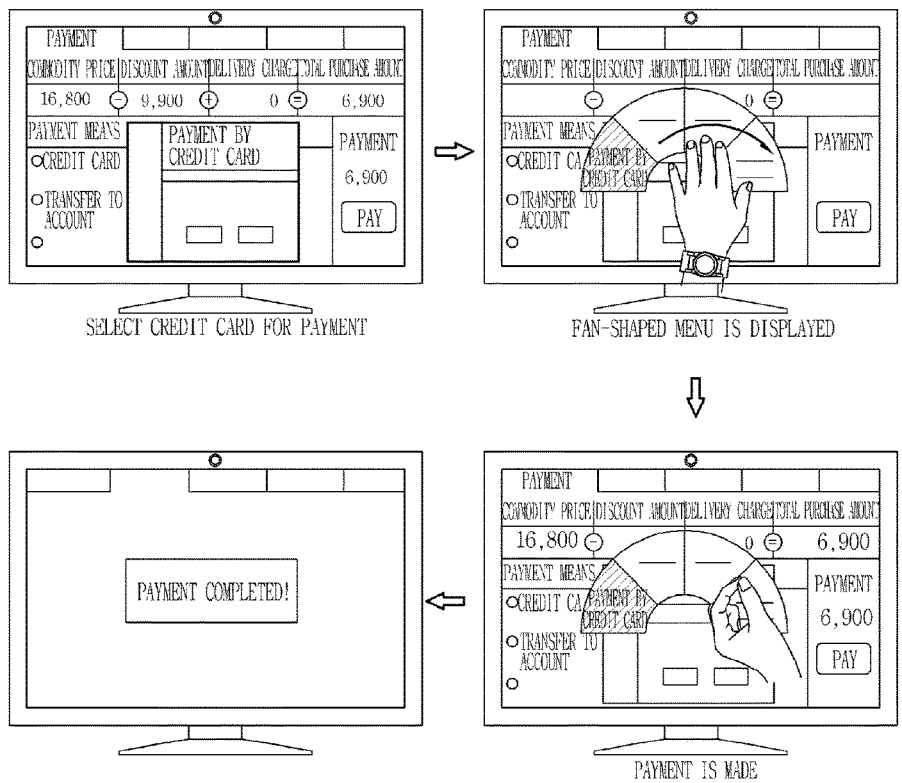

[Fig. 14b]
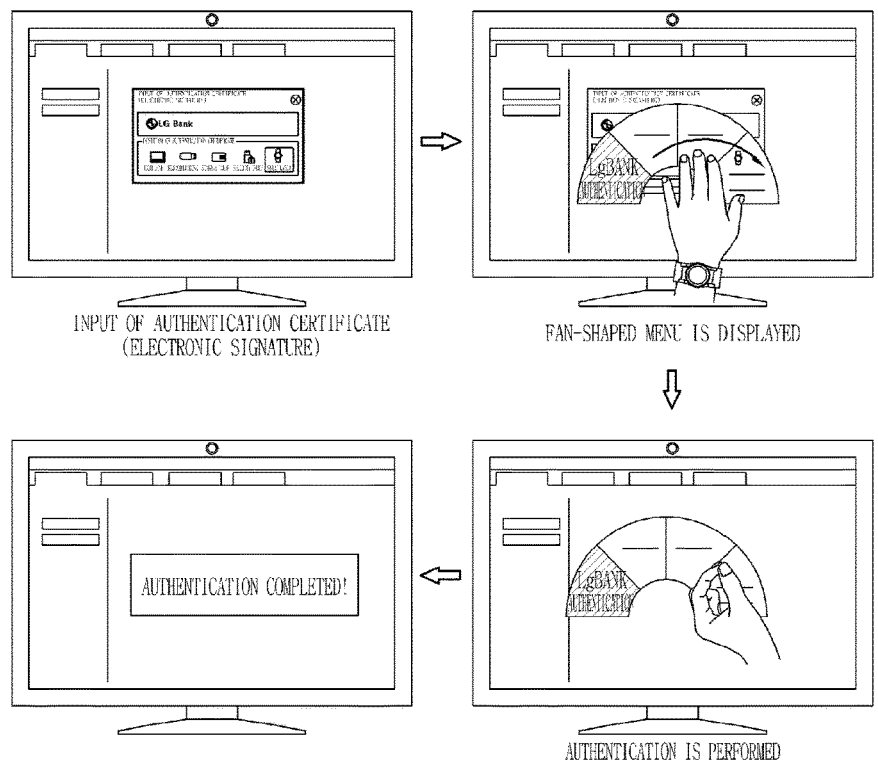
[Fig. 14c]
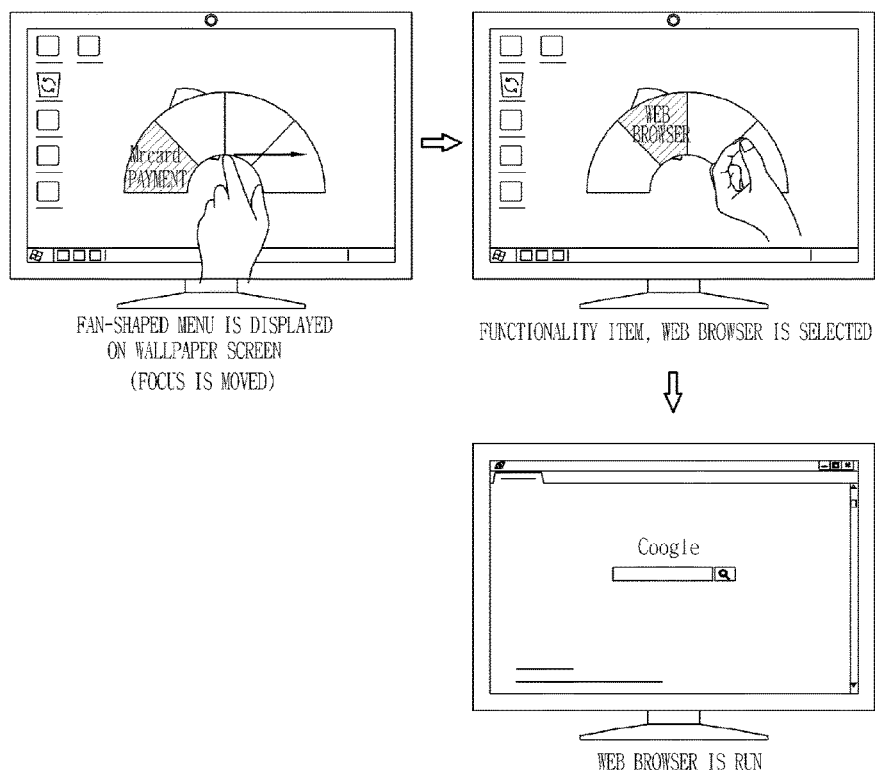

[Fig. 14d]
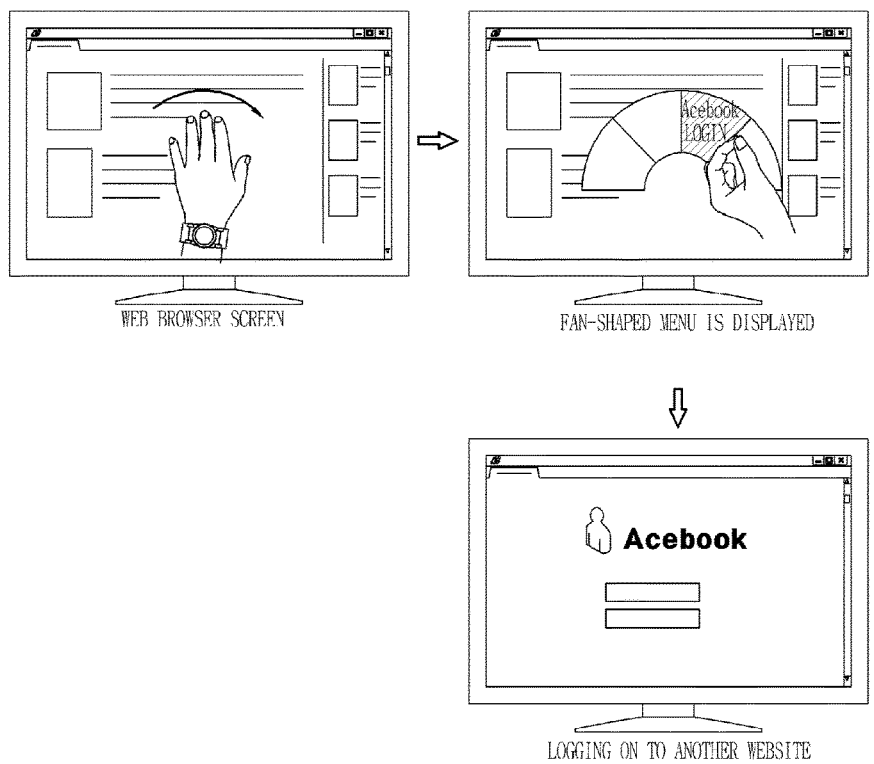
[Fig. 14e]
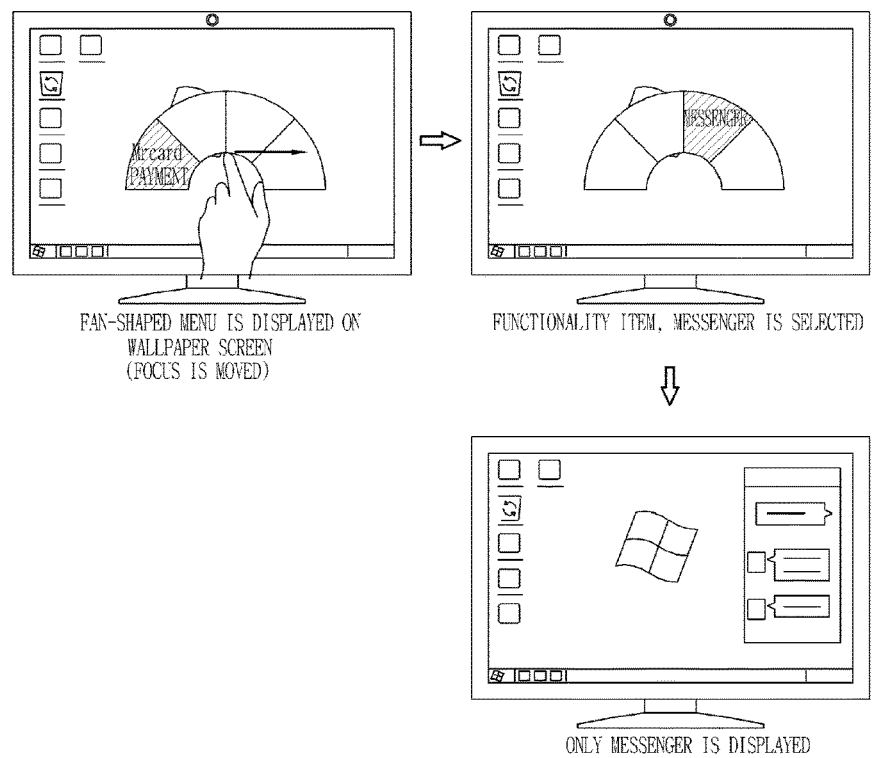

[Fig. 14f]
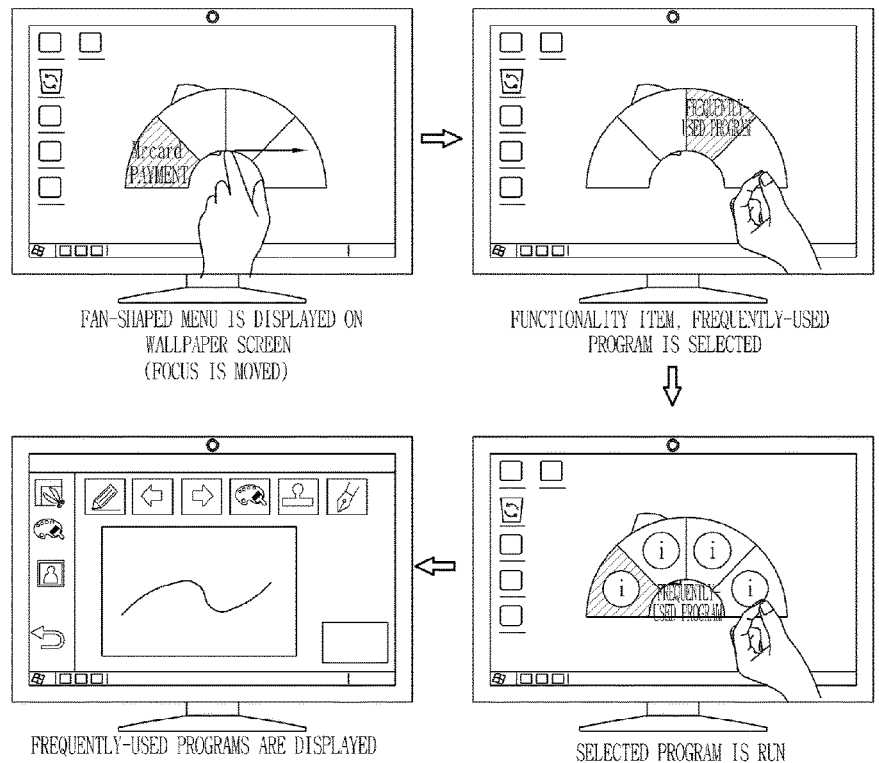
[Fig. 15a]
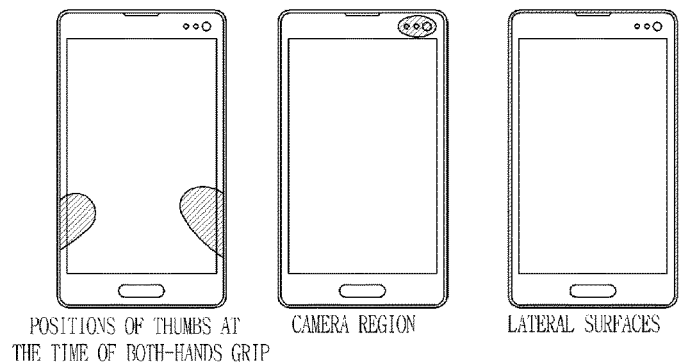
[Fig. 15b]
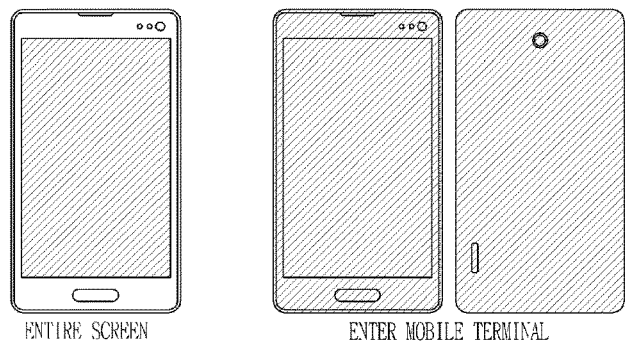

[Fig. 16a]
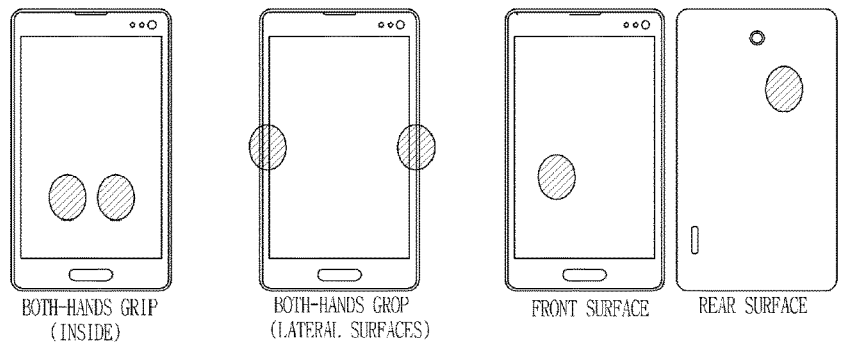
[Fig. 16b]
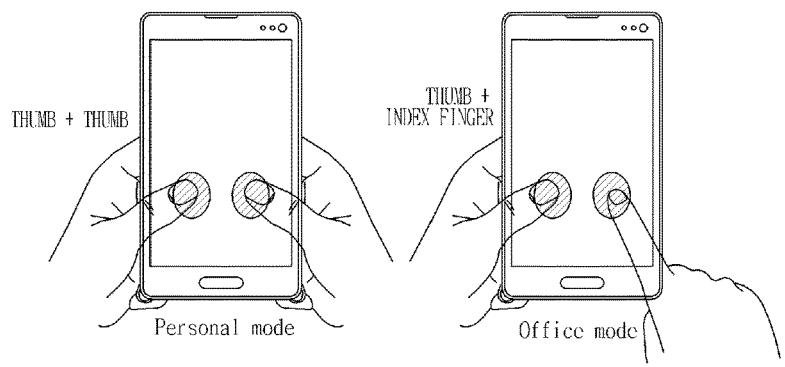
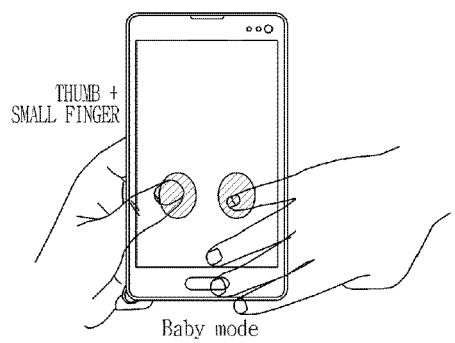
[Fig. 17]
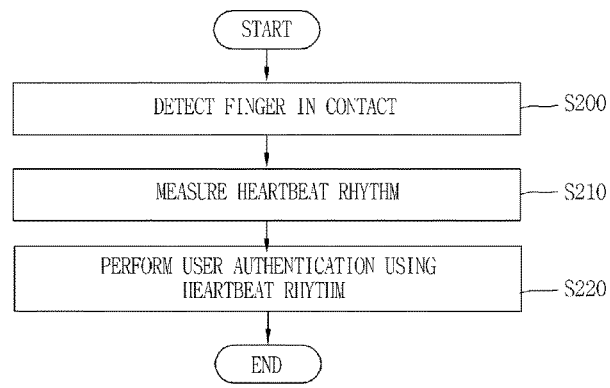

[Fig. 18]
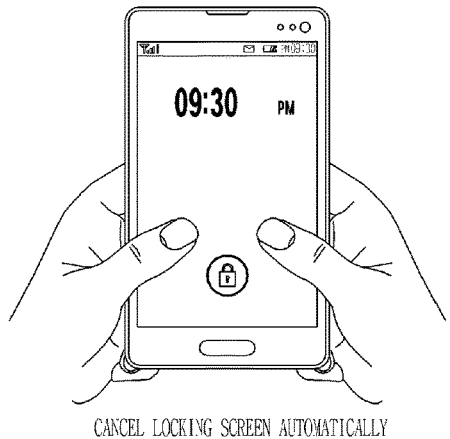
CANCEL LOCKING SCREEN AUTOMATICALLY
[Fig. 19]
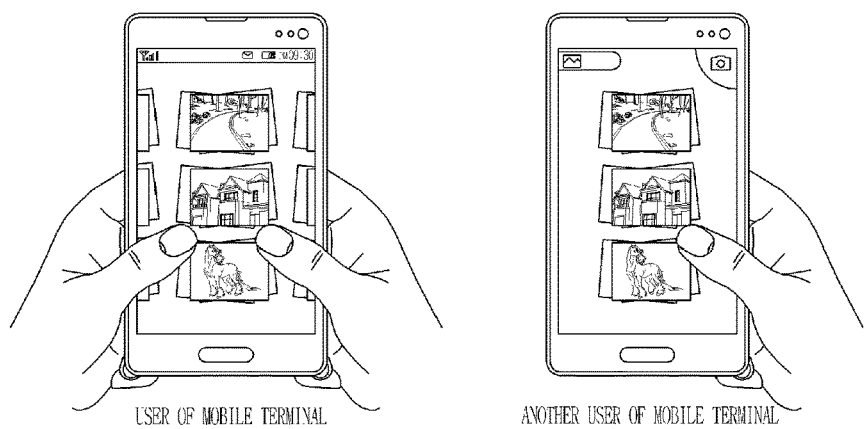
USER OF MOBILE TERMINAL    ANOTHER USER OF MOBILE TERMINAL
[Fig. 20a]
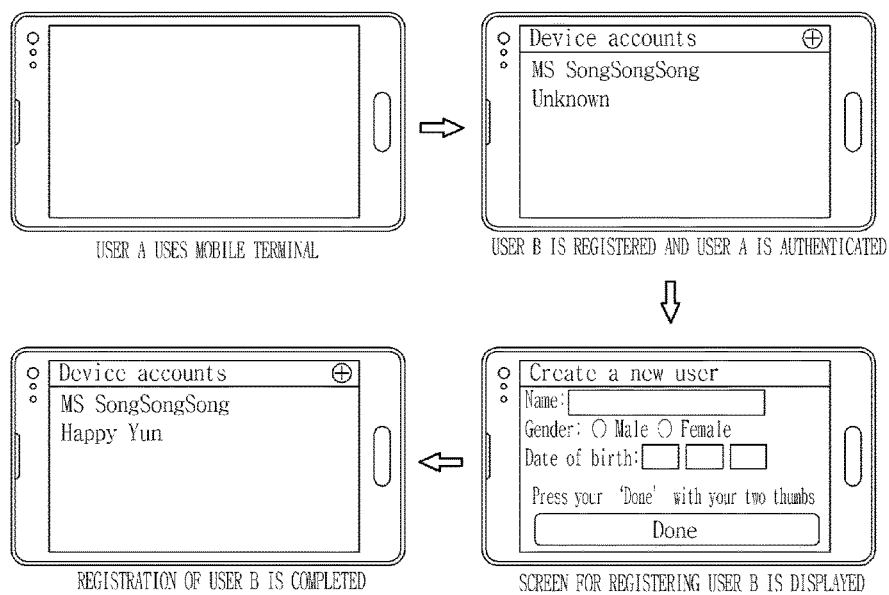

[Fig. 20b]
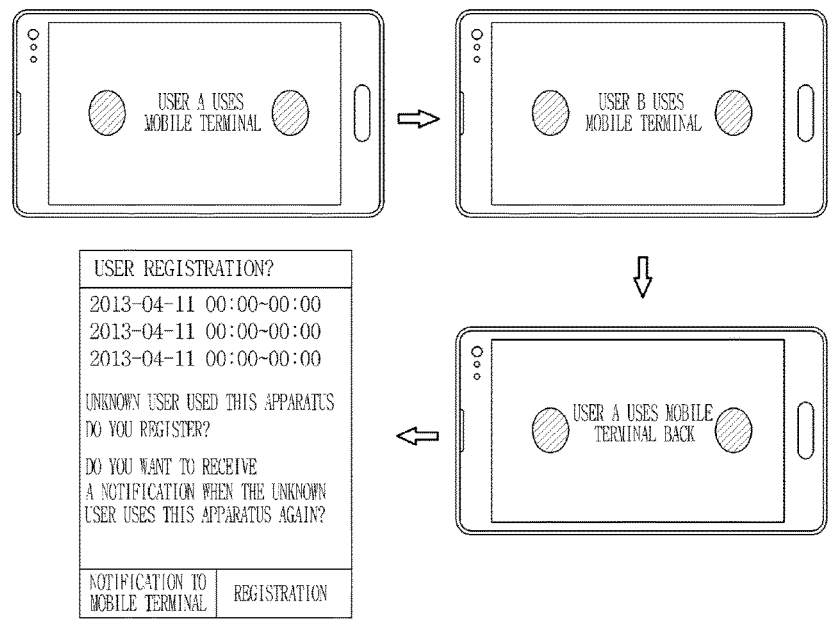
[Fig. 21]
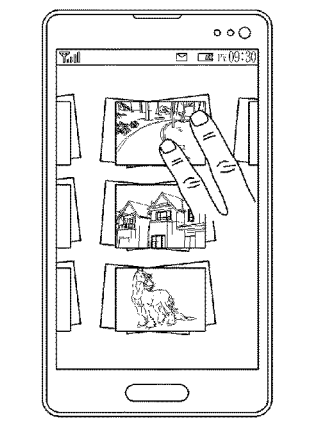
TWO TOUCHES ARE APPLIED TO FOLDER
(LOCKED STATE IS CANCELED)
[Fig. 22a]
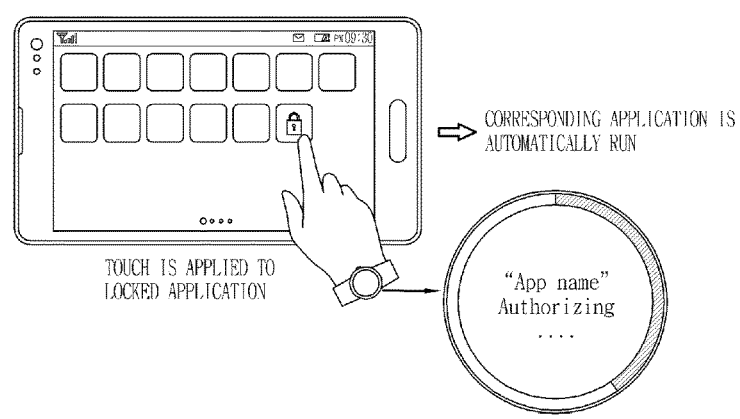

[Fig. 22b]
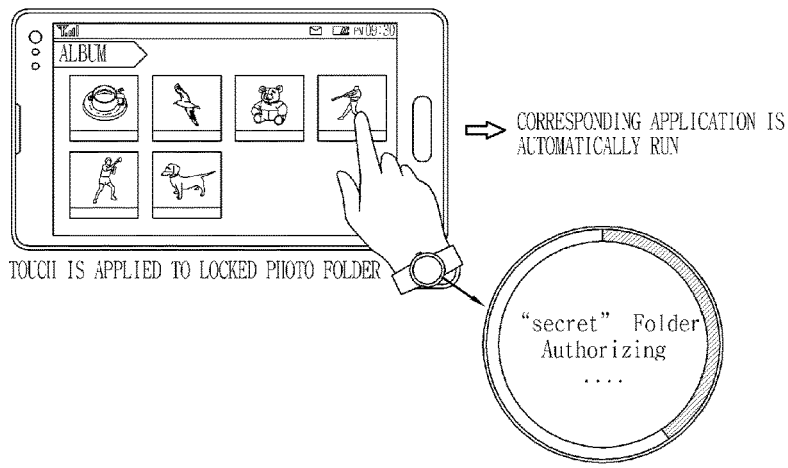
TOUCH IS APPLIED TO LOCKED PHOTO FOLDER
CORRESPONDING APPLICATION IS AUTOMATICALLY RUN
[Fig. 23]
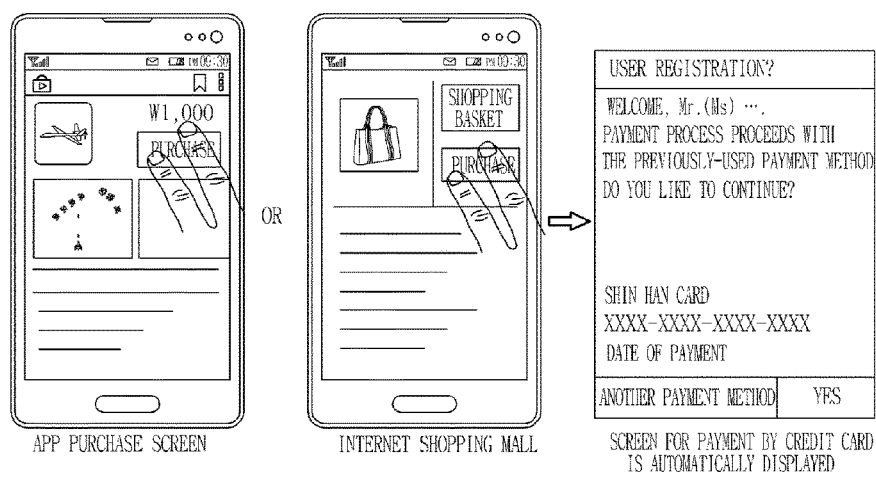
APP PURCHASE SCREEN
INTERNET SHOPPING MALL
SCREEN FOR PAYMENT BY CREDIT CARD IS AUTOMATICALLY DISPLAYED
[Fig. 24a]
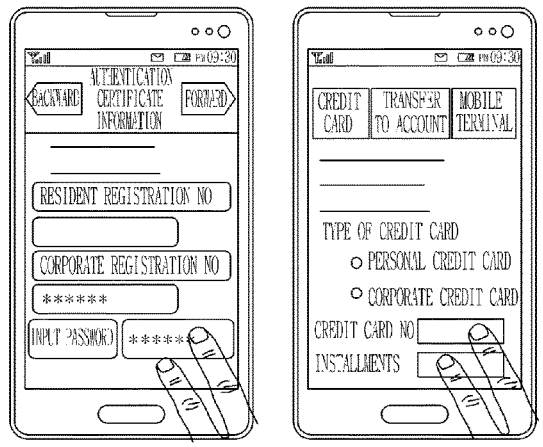
TWO TOUCHES ARE APPLIED TO REGION FOR INPUTTING PERSONAL INFORMATION (MOBILE TERMINAL)

[Fig. 24b]
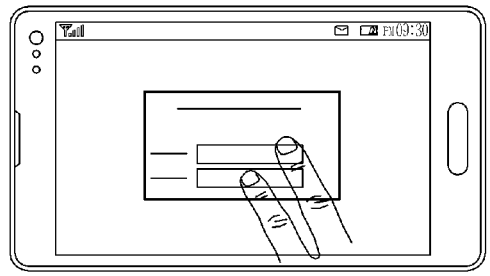
TWO TOUCHES ARE APPLIED TO REGION FOR
INPUTTING PERSONAL INFORMATION (TABLET PC)
[Fig. 24c]
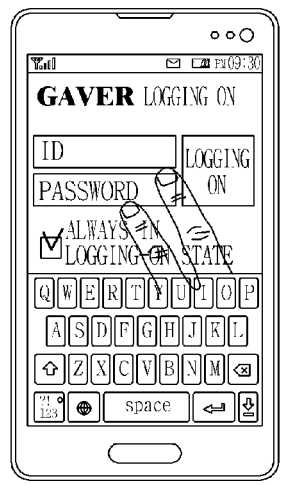 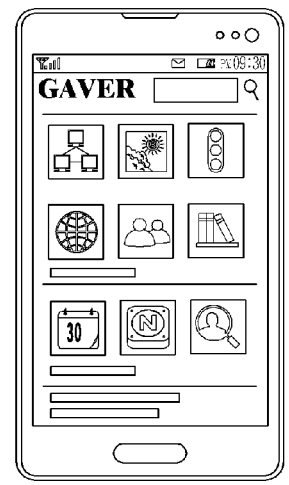
REGION FOR INPUTTING PASSWORD
TWO TOUCHES (MOBILE TERMINAL)
AUTOMATIC INPUTTING OF
PASSWORD AND LOGGING ON

MOBILE TERMINAL, SMART WATCH, AND METHOD OF PERFORMING AUTHENTICATION WITH THE MOBILE TERMINAL AND THE SMART WATCH

CROSS REFERENCE TO RELATED APPLICATIONS

This application is the National Phase of PCT International Application No. PCT/KR2014/006664, filed on Jul. 22, 2014, which claims priority to Patent Application No. KR 10-2013-0090453, filed in Republic of Korea on Jul. 30, 2013, all of which are hereby expressly incorporated by reference into the present application.

TECHNICAL FIELD

The present invention relates to a mobile terminal that is capable of conveniently performing user registration and authentication using a smart watch, and a method of performing authentication for security with the smart watch and the mobile terminal operating in conjunction.

BACKGROUND ART

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

Efforts are ongoing to support and increase the functionality of mobile terminals. Such efforts include software and hardware improvements, as well as changes and improvements in the structural components.

Generally, biometrics is a technology that authenticates or identifies a person by measuring physical or behavioral characteristics of the person with an automated apparatus. In recent years, the biometrics technology that uses the characteristics of the person, such as a fingerprint, a face, a palm print, a hand geometry, a retina, an iris, voice, and signature, has been developed and used. The biometrics technology that uses a blood vessel, DNA, and the like has been also under development. Accordingly, there is a rapidly-increasing concern in the biometrics. A standardization process in various fields for the biometrics technology makes rapid progress as well.

A heartbeat rhythm, among pieces of bio-information obtained using the biometrics technology, differs in frequency of vibration and waveform from user to user. For this reason, the heartbeat rhythm is valuably used in authenticating or identifying the person if the heartbeat rhythm is measured with the automated apparatus.

SUMMARY OF THE INVENTION

However, the Working Group (WG) for standardization of the biometrics technology has recently discussed only a standardization range and the like. Therefore, a current actual situation is that user authentication using bio-information, for example, the heartbeat rhythm, a method of controlling operation of a predetermined apparatus using biometric recognition when holding the predetermined apparatus in the hand or coming into contact with the predetermined apparatus, and a method of controlling various applications based on the method of controlling the operation of the predetermined apparatus haven't been provided.

Therefore, an aspect of the detailed description is to provide a mobile terminal that is capable of automatically performing user registration and authentication with application of biometrics technology to a smart watch, and a method of performing authentication with the smart watch and the mobile terminal operating in conjunction.

An another object of the present invention is to provide a smart watch that is capable of performing user registration and authentication using biometrics technology and a method of performing the authentication for security.

A further object of the present invention is to provide a mobile terminal that is capable of conveniently performing user registration and authentication with a smart watch and the mobile terminal operating in conjunction and a method of performing the authentication for security.

A still further object of the present invention is to provide a mobile terminal that is capable of control various function of the mobile terminal using a smart watch and a method of controlling operation of the mobile terminal.

To achieve these and other advantages and in accordance with the purpose of this specification, as embodied and broadly described herein, there is provided a method of performing authentication using a smart watch, including: detecting a request for authentication for executing an application; measuring a user's heartbeat rhythm through a sensor mounted in a bottom of the smart watch when detecting the request for the authentication; and comparing the measured heartbeat rhythm with an already-stored heartbeat rhythm and thus performing the authentication on the application.

In the method, the request for the authentication may be input into the smart watch or may be received from an external apparatus through a short-distance communication.

In the method, the external apparatus may be among a desktop computer, a laptop computer, a tablet computer, and a mobile terminal, and when the smart watch is selected as an authentication means, an authentication request signal may be transmitted to the smart watch.

In the method, the request for the authentication may occur when user authentication is selected from an authentication screen, the authentication screen may be a screen into which personal information on a user, and the authentication screens may include a payment screen for an on-line banking site and a on-line shopping mall, a web page, a logging-on screen for an application, a messenger and the like, and a locked screen for which a password is set In the method, a result of the user authentication may be displayed on a screen on the smart watch or is transmitted to the external apparatus for display, and the external apparatus may transmit the request for the authentication, along with information necessary for the authentication.

The method may further include controlling operation of the external apparatus according to a gesture that is made using a user's hand on which the smart watch is worn, with the smart watch and the external apparatus working in conjunction.

In the method, when the user's hand on which the smart watch is worn is moved in a predetermined direction while being opened, a fan-shaped menu for functionality items that are able to be performed with the smart watch and the external apparatus working in conjunction may be displayed on the external apparatus.

To achieve these and other advantages and in accordance with the purpose of this specification, as embodied and broadly described herein, there is provided a smart watch including: a display unit; a sensor that measures a user's heartbeat rhythm; and a controller that, when a request for authentication of a predetermined application is detected, compares the heartbeat rhythm measured in the sensor with an already-stored heartbeat rhythm and thus performs the authentication of the predetermined application.

In the smart watch, the request for the authentication may be input into the smart watch or may be received from an external apparatus through a short-distance communication.

In the smart watch, the external apparatus may be among a desktop computer, a laptop computer, a tablet computer, and a mobile terminal, and when the smart watch is selected as an authentication means, an authentication request signal may be transmitted to the smart watch.

In the smart watch, the request for the authentication may occur when user authentication is selected from an authentication screen, the authentication screen may be a screen into which personal information on a user, and the authentication screens may include a payment screen for a on-line banking site and an on-line shopping mall, a web page, a logging-on screen for an application, a messenger and the like, and a locked screen for which a password is set In the smart watch, the controller may display a result of the user authentication on a screen on the smart watch or transmits the result of the user authentication to the external apparatus, and the external apparatus may transmit the request for the authentication, along with information necessary for the authentication.

In the smart watch, the external apparatus may control operation of the application according to a gesture that is made using the user's hand on which the smart watch is worn, with the smart watch and the external apparatus working in conjunction.

In the smart watch, when the user's hand on which the smart watch is worn is moved in a predetermined direction while being opened, the external apparatus may display a fan-shaped menu for functionality items that are able to be performed with the smart watch and the external apparatus operating in conjunction.

In the smart watch, the external apparatus may include at least one or more sensors that senses a user's heartbeat rhythm, and the sensors may be positioned in a specific portion, the entire screen or the entire mobile terminal.

In the smart watch, when a specific grip type that is already stored is detected, the external apparatus may measure the user's heartbeat rhythm, thus automatically may perform the authentication, and thus displays a function screen that is frequently used, and the function screens may include a website, a game site, a bank website, and a cloud image folder.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

The present invention can perform a interworking function (e.g., the user registration/authentication between the smart watch and the mobile terminal by using the biometrics technology to the smart watch, and can conveniently control operations of the mobile terminal using the smart watch.

BRIEF DESCRIPTION OF DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings:

FIG. 1 is a block diagram illustrating a mobile terminal according to one embodiment of the present invention;

FIG. 2A is a block diagram illustrating a wireless communication system in which the mobile terminal according to one embodiment of the present invention operates;

FIG. 2B is a block diagram illustrating a Wi-Fi position tracking system in which the mobile terminal according to one embodiment of the present invention operates;

FIG. 3 is a diagram illustrating an example of a smart watch;

FIGS. 4A and 4B illustrate steps in which body information is measured and thus an authentication operation is performed when the smart watch according to an embodiment of the present invention is worn.

FIG. 5 is a flow chart illustrating a method of performing authentication using the smart watch according to the embodiment of the present invention;

FIGS. 6A and 6B illustrate that according to an embodiment, the authentication operation is performed using the smart watch;

FIG. 7 illustrates an example in which the authentication and money transfer business are performed on a bank website using the smart watch;

FIG. 8 illustrates an example in which the authentication is performed for payment by a credit card using the smart watch;

FIGS. 9A and 9B illustrate that according to an embodiment, the authentication and an account addition operation are performed when the smart watch is shared with other persons;

FIGS. 10A and 10B illustrate an example in which the smart watch is paired with a PC through such a technology as Bluetooth (BT) or NFC;

FIG. 11 is a flow chart illustrating a different function associated with the authentication, which is performed through the pairing of the smart watch with the PC;

FIG. 12 illustrates an example in which the authentication for logging onto the PC is performed using the smart watch;

FIG. 13 illustrates an example in which a fan-shaped menu is displayed using the smart watch;

FIGS. 14A to 14F illustrates that according to various embodiments, functionality items included in the fan-shaped menu are individually selected and performed;

FIGS. 15A to 15B indicates positions of an input unit for performing the authentication for security in the mobile terminal;

FIGS. 16A and 16B illustrate a method of performing the authentication for security according to an embodiment;

FIG. 17 is a flowchart for using bio-information and thus performing the authentication for security when the user holding in his/her hand or touches on the mobile terminal;

FIG. 18 illustrates that according to an embodiment, the user authentication is performed in an individual security mode;

FIG. 19 illustrates that according to another embodiment, the user authentication is performed in the individual security mode;

FIGS. 20A and 20B illustrate that according to an embodiment, the user authentication is performed in a multi-security mode;

FIG. 21 illustrates a method in which at the time of double locking, the authentication is performed;

FIGS. 22A and 22B are examples in which the authentication of an application on the mobile terminal is performed in the smart watch;

FIG. 23 illustrates an example in which automatic authentication and payment are performed at the time of Internet shopping; and FIGS. 24A to 24C illustrate that according to an embodiment, personal information is automatically input using the bio-information.

DETAILED DESCRIPTION OF EMBODIMENTS OF THE INVENTION

Description will now be given in detail according to the exemplary embodiments, with reference to the accompanying drawings. For the sake of brief description with reference to the drawings, the same or equivalent components will be provided with the same reference numbers, and description thereof will not be repeated. A suffix "module" or "unit" used for constituent elements disclosed in the following description is merely intended for easy description of the specification, and the suffix itself does not give any special meaning or function. In describing the present invention, if a detailed explanation for a related known function or construction is considered to unnecessarily divert the gist of the present disclosure, such explanation has been omitted but would be understood by those skilled in the art. The accompanying drawings are used to help easily understood the technical idea of the present invention and it should be understood that the idea of the present disclosure is not limited by the accompanying drawings.

Mobile terminals described herein may include cellular phones, smart phones, laptop computers, digital broadcasting terminals, personal digital assistants (PDAs), portable multimedia players (PMPs), navigators, slate PCs, tablet PC, ultra books and the like. However, it may be easily understood by those skilled in the art that the configuration according to the exemplary embodiments of this specification can be applied to stationary terminals such as digital TV, desktop computers and the like excluding a case of being applicable only to the mobile terminals.

FIG. 1 is a block diagram of a mobile terminal 100 in accordance with one exemplary embodiment.

The mobile terminal 100 may comprise components, such as a wireless communication unit 110, an Audio/Video (AN) input unit 120, a user input unit 130, a sensing unit 140, an output unit 150, a memory 160, an interface unit 170, a controller 180, a power supply 190 and the like. FIG. 1 shows the mobile terminal 100 having various components, but it is understood that implementing all of the illustrated components is not a requirement. Greater or fewer components may alternatively be implemented.

Hereinafter, each component is described in sequence.

The wireless communication unit 110 may typically include one or more modules which permit wireless communications between the mobile terminal 100 and a wireless communication system or between the mobile terminal 100 and a network within which the mobile terminal 100 is located. For example, the wireless communication unit 110 may include at least one of a broadcast receiving module 111, a mobile communication module 112, a wireless Internet module 113, a short-range communication module 114, a location information module 115 and the like.

The broadcast receiving module 111 receives a broadcast signal and/or broadcast associated information from an external broadcast managing entity via a broadcast channel.

The broadcast channel may include a satellite channel and a terrestrial channel. The broadcast managing entity may indicate a server which generates and transmits a broadcast signal and/or broadcast associated information or a server which receives a pre-generated broadcast signal and/or broadcast associated information and sends them to the mobile terminal. The broadcast signal may be implemented as a TV broadcast signal, a radio broadcast signal, and a data broadcast signal, among others. The broadcast signal may further include a data broadcast signal combined with a TV or radio broadcast signal.

Examples of broadcast associated information may include information associated with a broadcast channel, a broadcast program, a broadcast service provider, and the like. The broadcast associated information may be provided via a mobile communication network, and received by the mobile communication module 112.

The broadcast associated information may be implemented in various formats. For instance, broadcast associated information may include Electronic Program Guide (EPG) of Digital Multimedia Broadcasting (DMB), Electronic Service Guide (ESG) of Digital Video Broadcast-Handheld (DVB-H), and the like.

The broadcast receiving module 111 may be configured to receive digital broadcast signals transmitted from various types of broadcast systems. Such broadcast systems may include Digital Multimedia Broadcasting-Terrestrial (DMB-T), Digital Multimedia Broadcasting-Satellite (DMB-S), Media Forward Link Only (MediaFLO), Digital Video Broadcast-Handheld (DVB-H), Integrated Services Digital Broadcast-Terrestrial (ISDB-T) and the like. The broadcast receiving module 111 may be configured to be suitable for every broadcast system transmitting broadcast signals as well as the digital broadcasting systems.

Broadcast signals and/or broadcast associated information received via the broadcast receiving module 111 may be stored in a suitable device, such as a memory 160.

The mobile communication module 112 transmits/receives wireless signals to/from at least one of network entities (e.g., base station, an external mobile terminal, a server, etc.) on a mobile communication network. Here, the wireless signals may include audio call signal, video (telephony) call signal, or various formats of data according to transmission/reception of text/multimedia messages.

The mobile communication module 112 may implement a video call mode and a voice call mode. The video call mode indicates a state of calling with watching a callee's image. The voice call mode indicates a state of calling without watching the callee's image. The wireless communication module 112 may transmit and receive at least one of voice and image in order to implement the video call mode and the voice call mode.

The wireless Internet module 113 supports wireless Internet access for the mobile terminal. This module may be internally or externally coupled to the mobile terminal 100. Examples of such wireless Internet access may include Wireless LAN (WLAN) (Wi-Fi), Wireless Broadband (Wibro), Worldwide Interoperability for Microwave Access (Wimax), High Speed Downlink Packet Access (HSDPA) and the like.

The short-range communication module 114 denotes a module for short-range communications. Suitable technologies for implementing this module may include BLUETOOTH™, Radio Frequency IDentification (RFID), Infrared Data Association (IrDA), Ultra-WideBand (UWB), ZigBee™, Near Field Communication (NFC) and the like.

The location information module 115 denotes a module for detecting or calculating a position of a mobile terminal. An example of the location information module 115 may include a Global Position System (GPS) module.

Still referring to FIG. 1, the A/V input unit 120 is configured to provide audio or video signal input to the mobile terminal. The A/V input unit 120 may include a camera 121 and a microphone 122. The camera 121 receives and processes image frames of still pictures or video obtained by image sensors in a video call mode or a capturing mode. The processed image frames may be displayed on a display unit 151.

The image frames processed by the camera 121 may be stored in the memory 160 or transmitted to the exterior via the wireless communication unit 110. Also, user's position information and the like may be calculated from the image frames acquired by the camera 121. Two or more cameras 121 may be provided according to the configuration of the mobile terminal.

The microphone 122 may receive an external audio signal while the mobile terminal is in a particular mode, such as a phone call mode, a recording mode, a voice recognition mode, or the like. This audio signal is processed into digital data. The processed digital data is converted for output into a format transmittable to a mobile communication base station via the mobile communication module 112 in case of the phone call mode. The microphone 122 may include assorted noise removing algorithms to remove noise generated in the course of receiving the external audio signal.

The user input unit 130 may generate input data input by a user to control the operation of the mobile terminal. The user input unit 130 may include a keypad, a dome switch, a touchpad (e.g., static pressure/capacitance), a jog wheel, a jog switch and the like.

The sensing unit 140 provides status measurements of various aspects of the mobile terminal. For instance, the sensing unit 140 may detect an open/close status of the mobile terminal, a change in a location of the mobile terminal 100, a presence or absence of user contact with the mobile terminal 100, the location of the mobile terminal 100, acceleration/deceleration of the mobile terminal 100, and the like, so as to generate a sensing signal for controlling the operation of the mobile terminal 100. For example, regarding a slide-type mobile terminal, the sensing unit 140 may sense whether a sliding portion of the mobile terminal is open or closed. Other examples include sensing functions, such as the sensing unit 140 sensing the presence or absence of power provided by the power supply 190, the presence or absence of a coupling or other connection between the interface unit 170 and an external device.

The output unit 150 is configured to output an audio signal, a video signal or a tactile signal. The output unit 150 may include a display unit 151, an audio output module 153, an alarm unit 154 and a haptic module 155.

The display unit 151 may output information processed in the mobile terminal 100. For example, when the mobile terminal is operating in a phone call mode, the display unit 151 will provide a User Interface (UI) or a Graphic User Interface (GUI), which includes information associated with the call. As another example, if the mobile terminal is in a video call mode or a capturing mode, the display unit 151 may additionally or alternatively display images captured and/or received, UI, or GUI.

The display unit 151 may be implemented using, for example, at least one of a Liquid Crystal Display (LCD), a Thin Film Transistor-Liquid Crystal Display (TFT-LCD), an Organic Light-Emitting Diode (OLED), a flexible display, a three-dimensional (3D) display and an e-ink display.

Some of such displays 151 may be implemented as a transparent type or an optical transparent type through which the exterior is visible, which is referred to as transparent display. A representative example of the transparent display may include a Transparent OLED (TOLED), and the like. The rear surface of the display unit 151 may also be implemented to be optically transparent. Under this configuration, a user can view an object positioned at a rear side of a terminal body through a region occupied by the display unit 151 of the terminal body.

The display unit 151 may be implemented in two or more in number according to a configured aspect of the mobile terminal 100. For instance, a plurality of the displays 151 may be arranged on one surface to be spaced apart from or integrated with each other, or may be arranged on different surfaces.

The display unit 151 may also be implemented as a stereoscopic display unit 152 for displaying stereoscopic images.

Here, the stereoscopic image may be a three-dimensional (3D) stereoscopic image, and the 3D stereoscopic image is an image refers to an image making a viewer feel that a gradual depth and reality of an object on a monitor or a screen is the same as a reality space. A 3D stereoscopic image is implemented by using binocular disparity. Binocular disparity refers to disparity made by the positions of two eyes. When two eyes view different 2D images, the images are transferred to the brain through the retina and combined in the brain to provide the perception of depth and reality sense.

The stereoscopic display unit 152 may employ a stereoscopic display scheme such as stereoscopic scheme (a glass scheme), an auto-stereoscopic scheme (glassless scheme), a projection scheme (holographic scheme), or the like. Stereoscopic schemes commonly used for home television receivers, or the like, include Wheatstone stereoscopic scheme, or the like.

The auto-stereoscopic scheme includes, for example, a parallax barrier scheme, a lenticular scheme, an integral imaging scheme, or the like. The projection scheme includes a reflective holographic scheme, a transmissive holographic scheme, or the like.

In general, a 3D stereoscopic image is comprised of a left image (a left eye image) and a right image (a right eye image). According to how left and right images are combined into a 3D stereoscopic image, the 3D stereoscopic imaging method is divided into a top-down method in which left and right images are disposed up and down in a frame, an L-to-R (left-to-right, side by side) method in which left and right images are disposed left and right in a frame, a checker board method in which fragments of left and right images are disposed in a tile form, an interlaced method in which left and right images are alternately disposed by columns and rows, and a time sequential (or frame by frame) method in which left and right images are alternately displayed by time.

Also, as for a 3D thumbnail image, a left image thumbnail and a right image thumbnail are generated from a left image and a right image of the original image frame, respectively, and then combined to generate a single 3D thumbnail image. In general, thumbnail refers to a reduced image or a reduced still image. The thusly generated left image thumbnail and the right image thumbnail are displayed with a horizontal distance difference therebetween by a depth corresponding to the disparity between the left image and the right image on the screen, providing a stereoscopic space sense.

As illustrated, a left image and a right image required for implementing a 3D stereoscopic image is displayed on the stereoscopic display unit 152 by a stereoscopic processing unit (not shown). The stereoscopic processing unit may receive the 3D image and extract the left image and the right image, or may receive the 2D image and change it into a left image and a right image.

Here, if the display unit 151 and a touch sensitive sensor (referred to as a touch sensor) have a layered structure therebetween (referred to as a 'touch screen', the display unit 151 may be used as an input device as well as an output device. The touch sensor may be implemented as a touch film, a touch sheet, a touchpad, and the like.

The touch sensor may be configured to convert changes of a pressure applied to a specific part of the display unit 151, or a capacitance occurring from a specific part of the display unit 151, into electric input signals. Also, the touch sensor may be configured to sense not only a touched position and a touched area, but also touch pressure. Here, a touch object is an object to apply a touch input to the touch sensor. Examples of the touch object may include a finger, a touch pen, a stylus pen, a pointer or the like.

When touch inputs are sensed by the touch sensors, corresponding signals are transmitted to a touch controller. The touch controller processes the received signals, and then transmits corresponding data to the controller 180. Accordingly, the controller 180 may sense which region of the display unit 151 has been touched.

Still referring to FIG. 1, a proximity sensor 141 may be arranged at an inner region of the mobile terminal 100 covered by the touch screen, or near the touch screen. The proximity sensor 141 may be provided as one example of the sensing unit 140. The proximity sensor 141 indicates a sensor to sense presence or absence of an object approaching to a surface to be sensed, or an object disposed near a surface to be sensed, by using an electromagnetic field or infrared rays without a mechanical contact. The proximity sensor 141 has a longer lifespan and a more enhanced utility than a contact sensor.

The proximity sensor 141 may include a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and so on. When the touch screen is implemented as a capacitance type, proximity of a pointer to the touch screen is sensed by changes of an electromagnetic field. In this case, the touch screen (touch sensor) may be categorized into a proximity sensor.

Hereinafter, for the sake of brief explanation, a status that the pointer is positioned to be proximate onto the touch screen without contact will be referred to as 'proximity touch', whereas a status that the pointer substantially comes in contact with the touch screen will be referred to as 'contact touch'. For the position corresponding to the proximity touch of the pointer on the touch screen, such position corresponds to a position where the pointer faces perpendicular to the touch screen upon the proximity touch of the pointer.

The proximity sensor 141 senses proximity touch, and proximity touch patterns (e.g., distance, direction, speed, time, position, moving status, etc.). Information relating to the sensed proximity touch and the sensed proximity touch patterns may be output onto the touch screen.

When a touch sensor is overlaid on the stereoscopic display unit 152 in a layered manner (hereinafter, referred to as 'stereoscopic touch screen'), or when the stereoscopic display unit 152 and a 3D sensor sensing a touch operation are combined, the stereoscopic display unit 152 may also be used as a 3D input device.

As examples of the 3D sensor, the sensing unit 140 may include a proximity sensor 141, a stereoscopic touch sensing unit 142, an ultrasonic sensing unit 143, and a camera sensing unit 144.

The proximity sensor 141 detects the distance between a sensing object (e.g., the user's finger or a stylus pen) applying a touch by using the force of electromagnetism or infrared rays without a mechanical contact and a detect surface. By using the distance, the terminal recognizes which portion of a stereoscopic image has been touched. In particular, when the touch screen is an electrostatic touch screen, the degree of proximity of the sensing object is detected based on a change of an electric field according to proximity of the sensing object, and a touch to the 3D image is recognized by using the degree of proximity.

The stereoscopic touch sensing unit 142 is configured to detect the strength or duration of a touch applied to the touch screen. For example, the stereoscopic touch sensing unit 142 may sense touch pressure. When the pressure is strong, it may recognize the touch as a touch with respect to an object located farther away from the touch screen toward the inside of the terminal.

The ultrasonic sensing unit 143 is configured to recognize position information of the sensing object by using ultrasonic waves.

The ultrasonic sensing unit 143 may include, for example, an optical sensor and a plurality of ultrasonic sensors. The optical sensor is configured to sense light and the ultrasonic sensors may be configured to sense ultrasonic waves. Since light is much faster than ultrasonic waves, a time for which the light reaches the optical sensor is much shorter than a time for which the ultrasonic wave reaches the ultrasonic sensor. Therefore, a position of a wave generation source may be calculated by using a time difference from the time that the ultrasonic wave reaches based on the light as a reference signal.

The camera sensing unit 144 includes at least one of a camera, a photo sensor, and a laser sensor.

For example, the camera and the laser sensor may be combined to detect a touch of the sensing object with respect to a 3D stereoscopic image. When distance information detected by a laser sensor is added to a 2D image captured by the camera, 3D information can be obtained.

In another example, a photo sensor may be laminated on the mobile terminal. The photo sensor is configured to scan a movement of the sensing object in proximity to the touch screen. In detail, the photo sensor includes photo diodes and transistors at rows and columns to scan content mounted on the photo sensor by using an electrical signal changing according to the quantity of applied light. Namely, the photo sensor calculates the coordinates of the sensing object according to variation of light to thus obtain position information of the sensing object.

The audio output module 153 may convert and output as sound audio data received from the wireless communication unit 110 or stored in the memory 160 in a call signal reception mode, a call mode, a record mode, a voice recognition mode, a broadcast reception mode, and the like. Also, the audio output module 153 may provide audible outputs related to a particular function performed by the mobile terminal 100 (e.g., a call signal reception sound, a message reception sound, etc.). The audio output module 153 may include a speaker, a buzzer or the like.

The alarm unit 154 outputs a signal for informing about an occurrence of an event of the mobile terminal 100. Events generated in the mobile terminal may include call signal reception, message reception, key signal inputs, a touch input etc. In addition to video or audio signals, the alarm unit 154 may output signals in a different manner, for example, using vibration to inform about an occurrence of an event. The video or audio signals may be also outputted via the audio output module 153, so the display unit 151 and the audio output module 153 may be classified as parts of the alarm unit 154.

A haptic module 155 generates various tactile effects the user may feel. A typical example of the tactile effects generated by the haptic module 155 is vibration. The strength and pattern of the haptic module 155 can be controlled. For example, different vibrations may be combined to be outputted or sequentially outputted.

Besides vibration, the haptic module 155 may generate various other tactile effects such as an effect by stimulation such as a pin arrangement vertically moving with respect to a contact skin, a spray force or suction force of air through a jet orifice or a suction opening, a contact on the skin, a contact of an electrode, electrostatic force, etc., an effect by reproducing the sense of cold and warmth using an element that can absorb or generate heat.

The haptic module 155 may be implemented to allow the user to feel a tactile effect through a muscle sensation such as fingers or arm of the user, as well as transferring the tactile effect through a direct contact. Two or more haptic modules 155 may be provided according to the configuration of the mobile terminal 100.

The memory 160 may store software programs used for the processing and controlling operations performed by the controller 180, or may temporarily store data (e.g., a phonebook, messages, still images, video, etc.) that are inputted or outputted. In addition, the memory 160 may store data regarding various patterns of vibrations and audio signals outputted when a touch is inputted to the touch screen.

The memory 160 may include at least one type of storage medium including a Flash memory, a hard disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, and an optical disk. Also, the mobile terminal 100 may be operated in relation to a web storage device that performs the storage function of the memory 160 over the Internet.

The interface unit 170 serves as an interface with every external device connected with the mobile terminal 100. For example, the external devices may transmit data to an external device, receives and transmits power to each element of the mobile terminal 100, or transmits internal data of the mobile terminal 100 to an external device. For example, the interface unit 170 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating the authority of using the mobile terminal 100 and may include a user identity module (UIM), a subscriber identity module (SIM) a universal subscriber identity module (USIM), and the like. In addition, the device having the identification module (referred to as identifying device, hereinafter) may take the form of a smart card. Accordingly, the identifying device may be connected with the terminal 100 via the interface unit 170.

When the mobile terminal 100 is connected with an external cradle, the interface unit 170 may serve as a passage to allow power from the cradle to be supplied therethrough to the mobile terminal 100 or may serve as a passage to allow various command signals inputted by the user from the cradle to be transferred to the mobile terminal therethrough. Various command signals or power inputted from the cradle may operate as signals for recognizing that the mobile terminal is properly mounted on the cradle.

The controller 180 typically controls the general operations of the mobile terminal. For example, the controller 180 performs controlling and processing associated with voice calls, data communications, video calls, and the like. The controller 180 may include a multimedia module 181 for reproducing multimedia data. The multimedia module 181 may be configured within the controller 180 or may be configured to be separated from the controller 180.

The controller 180 may perform a pattern recognition processing to recognize a handwriting input or a picture drawing input performed on the touch screen as characters or images, respectively.

Also, the controller 180 may execute a lock state to restrict a user from inputting control commands for applications when a state of the mobile terminal meets a preset condition. Also, the controller 180 may control a lock screen displayed in the lock state based on a touch input sensed on the display unit 151 in the lock state of the mobile terminal.

The power supply unit 190 receives external power or internal power and supplies appropriate power required for operating respective elements and components under the control of the controller 180.

Various embodiments described herein may be implemented in a computer-readable or its similar medium using, for example, software, hardware, or any combination thereof.

For hardware implementation, the embodiments described herein may be implemented by using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic units designed to perform the functions described herein. In some cases, such embodiments may be implemented by the controller 180 itself.

For software implementation, the embodiments such as procedures or functions described herein may be implemented by separate software modules. Each software module may perform one or more functions or operations described herein.

Software codes can be implemented by a software application written in any suitable programming language. The software codes may be stored in the memory 160 and executed by the controller 180.

Hereinafter, a communication system which is operable with the mobile terminal 100 according to the present disclosure will be described.

FIGS. 2A and 2B are conceptual views of a communication system operable with a mobile terminal 100 in accordance with the present disclosure.

First, referring to FIG. 2A, such communication systems utilize different air interfaces and/or physical layers. Examples of such air interfaces utilized by the communication systems include Frequency Division Multiple Access (FDMA), Time Division Multiple Access (TDMA), Code Division Multiple Access (CDMA), and Universal Mobile Telecommunications System (UMTS), the Long Term Evolution (LTE) of the UMTS, the Global System for Mobile Communications (GSM), and the like.

By way of non-limiting example only, further description will relate to a CDMA communication system, but such teachings apply equally to other system types including the CDMA wireless communication system.

Referring now to FIG. 2A, a CDMA wireless communication system is shown having a plurality of mobile terminal s 100, a plurality of base stations (BSs) 270, base station controllers (BSCs) 275, and a mobile switching center (MSC) 280. The MSC 280 is configured to interface with a conventional Public Switch Telephone Network (PSTN) 290. The MSC 280 is also configured to interface with the BSCs 275. The BSCs 275 are coupled to the base stations 270 via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs 275 can be included in the system as shown in FIG. 2A.

Each base station 270 may include one or more sectors, each sector having an omnidirectional antenna or an antenna pointed in a particular direction radially away from the base station 270. Alternatively, each sector may include two or more different antennas. Each base station 270 may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations 270 may also be referred to as Base Station Transceiver Subsystems (BTSs). In some cases, the term "base station" may be used to refer collectively to a BSC 275, and one or more base stations 270. The base stations may also be denoted as "cell sites." Alternatively, individual sectors of a given base station 270 may be referred to as cell sites.

A broadcasting transmitter (BT) 295, as shown in FIG. 2A, transmits a broadcast signal to the mobile terminal s 100 operating within the system. The broadcast receiving module 111 (FIG. 1B) is typically configured inside the mobile terminal 100 to receive broadcast signals transmitted by the BT 295.

FIG. 2A further depicts several Global Positioning System (GPS) satellites 300. Such satellites 300 facilitate locating the position of at least one of plural mobile terminal s 100. Two satellites are depicted in FIG. 2, but it is understood that useful position information may be obtained with greater or fewer satellites than two satellites. The GPS module 115 (FIG. 1B) is typically configured to cooperate with the satellites 300 to obtain desired position information. It is to be appreciated that other types of position detection technology, (i.e., location technology that may be used in addition to or instead of GPS location technology) may alternatively be implemented. If desired, at least one of the GPS satellites 300 may alternatively or additionally be configured to provide satellite DMB transmissions.

During typical operation of the wireless communication system, the base stations 270 receive sets of reverse-link signals from various mobile terminal s 100. The mobile terminal s 100 are engaging in calls, messaging, and executing other communications. Each reverse-link signal received by a given base station 270 is processed within that base station 270. The resulting data is forwarded to an associated BSC 275. The BSC 275 provides call resource allocation and mobility management functionality including the orchestration of soft handoffs between base stations 270. The BSCs 275 also route the received data to the MSC 280, which then provides additional routing services for interfacing with the PSTN 290. Similarly, the PSTN 290 interfaces with the MSC 280, and the MSC 280 interfaces with the BSCs 275, which in turn control the base stations 270 to transmit sets of forward-link signals to the mobile terminal s 100.

Hereinafter, description will be given of a method for acquiring location information of a mobile terminal using a wireless fidelity (WiFi) positioning system (WPS), with reference to FIG. 2B.

The WiFi positioning system (WPS) 300 refers to a location determination technology based on a wireless local area network (WLAN) using WiFi as a technology for tracking the location of the mobile terminal 100 using a WiFi module provided in the mobile terminal 100 and a wireless access point 320 for transmitting and receiving to and from the WiFi module.

The WiFi positioning system 300 may include a WiFi location determination server 310, a mobile terminal 100, a wireless access point (AP) 320 connected to the mobile terminal 100, and a database 330 stored with any wireless AP information.

The WiFi location determination server 310 extracts the information of the wireless AP 320 connected to the mobile terminal 100 based on a location information request message (or signal) of the mobile terminal 100. The information of the wireless AP 320 may be transmitted to the WiFi location determination server 310 through the mobile terminal 100 or transmitted to the WiFi location determination server 310 from the wireless AP 320.

The information of the wireless AP extracted based on the location information request message of the mobile terminal 100 may be at least one of MAC address, SSID, RSSI, channel information, privacy, network type, signal strength and noise strength.

The WiFi location determination server 310 receives the information of the wireless AP 320 connected to the mobile terminal 100 as described above, and compares the received wireless AP 320 information with information contained in the pre-established database 330 to extract (or analyze) the location information of the mobile terminal 100.

On the other hand, referring to FIG. 2B, as an example, the wireless AP connected to the mobile terminal 100 is illustrated as a first, a second, and a third wireless AP 320. However, the number of wireless APs connected to the mobile terminal 100 may be changed in various ways according to a wireless communication environment in which the mobile terminal 100 is located. When the mobile terminal 100 is connected to at least one of wireless APs, the WiFi positioning system 300 can track the location of the mobile terminal 100.

Next, considering the database 330 stored with any wireless AP information in more detail, various information of any wireless APs disposed at different locations may be stored in the database 330.

The information of any wireless APs stored in the database 330 may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like.

In this manner, any wireless AP information and location information corresponding to the any wireless AP are stored together in the database 330, and thus the WiFi location determination server 310 may retrieve wireless AP information corresponding to the information of the wireless AP 320 connected to the mobile terminal 100 from the database 330 to extract the location information matched to the searched wireless AP, thereby extracting the location information of the mobile terminal 100.

Furthermore, the extracted location information of the mobile terminal may be transmitted to the mobile terminal 100 through the WiFi location determination server 310, thereby acquiring the location information of the mobile terminal 100.

According to the present invention, a method is provided in which, by applying bio-information obtained using a biometrics technology, particularly heartbeat rhythm that varies from one user to another, to a smart watch, user registration/authentication is performed and various operations by a mobile terminal are controlled.

Bio-information includes information on a human living body (a face, a palm print, a fingerprint, an iris, and the like) and information (a heart rate, an amount of flowing blood, and the like) that is generated in the human living body. Particularly, according to the present invention, automatic authentication is performed using information, such as the heartbeat rhythm, that is measurable when one portion (a hand, a finger, a wrist, and the like) of a user's body comes into contact with a smart watch or an external apparatus (for example, a mobile terminal) that is equipped with a sensor which measures the bio-information.

According to the present invention, at least one or more sensors are provided to measure the heartbeat rhythm. The sensors are provided in one or more, or all, of the front surface, the rear surface, and the four lateral surfaces of the mobile terminal. The sensor is mounted in a portion of the smart watch that comes into direct contact with the living body, such as the bottom of the smart watch.

The automatic authentication is performed when one portion (the hand, the finger, the wrist, and the like) of the user's body comes into contact with the surface in which the sensor is mounted, in order for the user to perform a predetermined task with the mobile terminal, and particularly the automatic authentication is performed in the background.

FIG. 3 illustrates one example of the smart watch.

Referring to FIG. 3, the smart watch is in the form of a watch into which functions of the mobile terminal are embedded. The smartphone is small in size, but has a configuration the same configuration (including a controller, a memory, a display unit, a communication unit, and the like) as the mobile terminal. Therefore, the smart watch is not an apparatus that is different from the mobile terminal, and is one type of mobile terminal that is shape-different.

At least one or more sensors for measuring body information are mounted in a bottom 50 of the smart watch. This is so because the smart watch is worn on the wrist and thus the mounting of the sensor in the bottom (rear side) of the watch is most advantageous to the measuring of the body information. In the case of the mobile terminal, the body information is measured when the mobile terminal is gripped with the hand or is touched on. However, the sensor is not positioned fixedly in the bottom of the sensor and may be mounted in other portions of the sensor whenever necessary.

Therefore, when the user applies a long touch to a screen for a predetermined time in a state where the user wears the smart watch on the wrist, the sensor that comes into contact with the skin measures the bio-information on the user.

FIGS. 4A and 4B illustrate steps in which the body information is measured and thus an authentication operation is performed when the smart watch according to the embodiment of the present invention is worn.

As illustrated in FIG. 4A, the user goes to an initial registration screen through a menu in a state where he/she wears the smart watch on the wrist. The long touch is applied to the initial registration screen for a predetermined time (about three seconds), the sensor mounted in the bottom of the smart watch measures the information on the user's body (for example, the heartbeat rhythm).

When the measuring is completed, the measured body is displayed on the screen, and a message asking whether or not the body information is to be registered is displayed. The use pushes down a confirmation button to register the body information, and when the body information is registered, a completion message (for example, "Hi, Samara") is displayed. Whether or not a result of the measuring is displayed can be selected.

Therefore, as illustrated in FIG. 4B, the user can perform user authentication by applying the long touch when authentication or generation of a one-time password (OTP) is necessary to perform banking-related business (e.g. remittance) or data transmission using the smart watch. When the long touch is applied to the screen, the controller 180 compares the bio-information measured in the smart watch with already-stored bio-information, performs the user authentication, and thus displays a result of the authentication on the screen.

FIG. 5 is a flow chart illustrating an authentication method of performing the authentication using the smart watch according to the embodiment of the present invention.

The smart watch is connected to a PC or the mobile terminal through short-distance communication. When an authentication request is detected in the state in which the user wears the smart watch (S100), the controller (not illustrated) of the smart watch measures the user's heartbeat rhythm through the sensor mounted in the bottom of the smart watch and then performs the authentication by comparison with a registered heartbeat rhythm (S110).

The authentication request is input from the smart watch directly by the user or is received from the PC or the mobile terminal through the short-distance communication using a technology such as Bluetooth (BT) or NFC.

The authentication request takes place when the user selects an authentication operation from an authentication screen. The authentication screen is a screen that is necessary for the user authentication. The authentication screens, for example, include screens into which user's personal information is input, such as a payment screen for an on-line banking site and an on-line shopping mall, a web page, a logging-on screen for an application, a messenger and the like, and a locked screen for which a password is set. The personal information includes an authentication certificate, a password, a credit card number, an account number, ID, and the like.

When the user authentication is completed, the result of the authentication is displayed on a screen (display unit) of the smart watch (S120). The result of the authentication is displayed on the screen of the smart watch, or is transmitted to the PC or the mobile terminal for display, and is displayed corresponding to the currently-displayed authentication screen. Particularly, when the authentication request is made to the smart watch, the PC or the mobile terminal transmits information (e.g., payment information or money transfer information), along with the authentication request.

FIGS. 6A and 6B illustrate that according to an embodiment, the authentication operation is performed using the smart watch. FIG. 6A illustrates the example in which when the user visits a bank website, the authentication operation is performed using the smart watch. FIG. 6B illustrates a bank authentication certificate screen.

The smart watch according to the present invention performs communication with another apparatus (a PC, a mobile terminal, or a notebook computer) over a short-range communication network, and thus performs the authentication operation on an application that is run on each apparatus.

After according to the authentication request of each apparatus, the information on the user's body (e.g., the heartbeat rhythm or the heart rate) is measured through the sensor mounted in one side of the smart watch, the user authentication is performed by comparing the measured information with the already-registered body information. The user authentication includes user authentication necessary for handling a banking-related business (e.g., remittance), paying an amount of a purchase order with the credit card, and logging onto a predetermined website or an application.

Referring to FIG. 6A, when a connection to a web page of a specific bank (for example, WOORI BANK) through the PC and then the smart watch is selected as an authentication means from an authentication certificate screen 51 as illustrated in FIG. 6B, the authentication request is made to the smart watch.

The controller (not illustrated) of the smart watch that receives the authentication request displays a screen for searching for an authentication certificate for a WOORI BANK and searches for the authentication certificate. When searching for the already-stored authentication certificate is completed, the controller displays the fact that the already-stored authentication certificate is completed. If the smart watch does not keep in close contact with the wrist, a message requesting for the close contact with the wrist, for example, "Please keep the rear side of the watch in close contact with the wrist" is displayed. If a predetermined area or above of the smart watch keeps in close contact with the wrist, the message requesting for the close contact with the wrist is not further displayed.

The user keeps the smart watch in close contact with the wrist according to the requesting message. If the smart watch comes into close contact with the wrist, the controller outputs sound notifying the fact that the smart watch keeps in close contact with the wrist.

Once the smart watch keeps in close with the wrist, the controller performs the user authentication by measuring the user's heartbeat rhythm through the sensor, and displays "in process" indicating that the user authentication is currently in process, on the screen.

When the user authentication is completed, the controller of the smart watch displays the result of performing the user the authentication is displayed on the screen, and automatically transmits the result of the authentication to the PC.

According to an authentication completion signal that is transmitted from the smart watch, the PC switches the screen and displays a logging-on completion page.

FIG. 7 illustrates an example in which the authentication and money transfer business are performed on the bank website using the smart watch.

When the user visits the bank website through the PC and then performs the money transfer to an account in a different bank, the user can perform the user authentication for the money transfer to the different account.

That is, when an amount of remittance and a remittance account number are input on a money transfer screen and then a confirmation button is selected or the smart watch is selected as a payment means, money transfer information (an account owner, a name of a receiving bank, the amount of remittance and the remittance account number) is automatically displayed on a screen of the smart watch. In this case, the PC transmits the money transfer information, along with the authentication request.

When the user selects the confirmation button, the heartbeat rhythm is measured and thus the user authentication is performed. However, if the smart watch does not keep in close contact with the wrist, the message requesting for the close contact with the wrist is output. When the user authentication is completed with the heartbeat rhythm, additional authentication is performed such as inputting a password, using a security card, and performing certified authentication. When the authentication operation described above is completed, the controller of the smart watch displays a result of the money transfer to the account in the different bank on the screen.

FIG. 8 illustrates an example in which the authentication is performed for payment by a credit card using the smart watch.

When a watch credit card is selected as a credit card for payment in a state where the smart watch is worn, a credit card selection screen is displayed on a screen on the smart watch, along payment information. A specific credit card for payment (e.g., MASTER CARD" is selected from the credit card selection screen, the controller of the smart watch measures the heartbeat rhythm, performs credit card authentication, and performs payment process, that is, performs payment with the selected credit card. Then, the controller of the smart watch displays a result of the payment.

FIG. 9A illustrates that according to an embodiment, authentication and an account addition operation are performed when the smart watch is shared with other persons.

An email service provides multi accounts for two or more users, that is, for family members. For example, multi accounts, that is, xx@live.com and yy@hotmail.com are set and then each user logs onto his/her account to use the email service.

Therefore, when logging onto each account from the smartphone or the PC, the user authentication is performed on the corresponding account through the smart watch. That is, as illustrated in FIG. 9A, when a different user whose account is added wears the smartphone in a state where the logging-on screen is displayed, the different user's heartbeat rhythm is automatically is measured, and logging onto the different user's account then takes place automatically.

However, as illustrated in FIG. 9B, when a user whose account is not added (set) wears the smart watch, a message that the wearer is a unknown user is displayed on the screen on the smart watch. When the long touch is applied to the screen on the smart watch, the heartbeat rhythm is measured and then an account can be added.

According to the present invention, when a specific user wears the smart watch, the user's heartbeat rhythm is automatically measured through a body information sensor to identify the user. In addition, the moment the smart watch according to the present invention is worn, or when a specific authentication operation is performed, it is verified with the heartbeat rhythm whether or not the wearer is a registered user.

FIGS. 10A and 10B illustrate an example in which the smart watch is paired with the PC through such a technology as Bluetooth (BT) or NFC.

As illustrated in FIG. 10A, if the smartphone have not been connected to the PC, when the user waves his/her hand on which the smart watch is worn, from left to right, a BT mode in which the smart watch is connected to the PC is activated and then a connection assistance message is displayed.

In addition, as illustrated in FIG. 10B, if the smart watch has not been connected to the PC, when the user waves his/her hand on which the smart watch is worn, from left to right, an NFC function works and an NFC mode in which the smart watch is connected to the PC is activated. Then, the connection assistance message is displayed.

The activation of the BT mode or the NFC mode is selected from a menu. When a confirmation button (for example, YES) is selected from the connection assistance message, the smart watch is connected to the PC and the authentication is performed through the smart watch, and the user can control operation of the PC with his/her hand, such as with an air mouse. For example, when after the smart watch is connected to the PC, the user rightward waves his/her hand on which the smart watch is worn, the next page is displayed.

Therefore, according to the present invention, the smart watch is paired with the PC through the short-distance communication (BT or NFC) and thus the authentication and other function associated with the authentication are performed, FIG. 11 is a flow chart illustrating a different function associated with the authentication, which is performed through the pairing of the smart watch with the PC.

As illustrated in FIG. 11, when the user authentication is performed through the smart watch, a control unit of the PC recognizes a user's gesture and thus displays a menu for functionality items that can be performed with the smart watch and the PC operating in conjunction (S200 to S220).

The gesture includes, for example, a leftward-to-rightward motion of the user's hand on which the smart watch is worn. The functionality items that can be performed through the pairing of the smart watch with the PC include operational control (e.g., powering off and logging-out) of the PC, authentication and payment, a Web browser connection, a messenger, and a frequently-used program.

The user selects a specific functionality item from the menu and then gives a command to perform a desired function using a simple selection gesture such as a finger snapping, and the control unit of the PC performs the corresponding function (S230).

FIG. 12 illustrates an example in which the authentication for logging onto the PC is performed using the smart watch.

When the user who wears the smart watch waves his/her opened hand in front of the screen on a monitor of the PC as if he/she says hello, he/she logs directly onto a wallpaper screen without having to go through a logging-on process. That is, the control unit of the PC automatically performs the logging-on according to a motion of the user's hand recognized through a PC camera 60 and a result of the authentication using the smart watch.

Therefore, if the smart watch is already connected to the PC, when the user who wears the smart watch waves his/her hand in front of the logging-on screen, such a hand gesture is recognized through the camera and thus the logging-on is automatically performed.

When the user waves his/her hand once more in the logged-onto state, a pop-up window for selecting a logging-off function, a power-off function, and a cancellation function. The user selects a button with a motion of his/her hand such as with the air mouse and then snaps his/her finger to perform one function, among the logging-off function, the power-off function and the cancellation function.

According to the present invention, when the smart watch is brought into contact with the PC in a state where a predetermined screen is displayed, a menu for performing a function associated with the state where the predetermined screen is displayed. The menu is a fan-shaped menu that is used in the smart watch, and includes a program optimized for the smart watch.

FIG. 13 illustrates an example in which the fan-shaped menu is displayed using the smart watch.

As illustrated in FIG. 13, when in front of the wallpaper screen, the user opens his/her hand on which the smart watch is worn and moves his/her opened hand from left to right, the fan-shaped menu for functionality items that can be performed with the smart watch and the PC operating in conjunction is displayed on the screen on the PC.

The fan-shaped menu is a menu that is used mainly in the smart watch. The fan-shaped menu includes one or more functionality items that can launch a program. The functionality items include authentication and payment (a credit card, a bank authentication certificate, an OTP, and the like) using the personal information, a Web browser (bookmark), a messenger and a frequently-used program. When the hand is waved in the opposite direction (from right to left), the fan-shaped menu disappears.

The user successively moves his/her hand in a predetermined direction (rightward or leftward) in the state where the fan-shaped menu is displayed, selects a desired functionality item, and thus performs the selected functionality item with the finger snapping. Therefore, the user performs the authentication and payment (the credit card, the bank authentication certificate, the OPT and the like), the web browser, the messenger, and the frequently-used selectively from the fan-shaped menu.

According to the present invention, control operation is performed not only from the wallpaper screen, but also from the web page or the bank website, using the smart watch.

FIGS. 14A to 14E illustrate that according to various embodiments, the functionality items included in the fan-shaped menu are individually selected and performed.

The user establishes a connection to a predetermined web page, for example, a shopping mall site through the PC and purchases a desired product. In this case, the user can conveniently pay for the desired product through interworking between the smart watch and the PC without having to input the personal information and the credit card information in detail for payment.

Referring to FIG. 14A, the fan-shaped menu is displayed when in a state where a payment page of a predetermined web page (shopping mall site) is displayed on the screen on the PC, the user waves his/her hand on which the smart watch is worn, from right to left. In this case, an authentication and payment menu currently associated with the payment page is previously in focus on the fan-shaped menu. If a specific credit card has been selected for payment, the specific credit card (for example, HYUNDAI CARD) is automatically displayed.

The user can select a desired credit card from the authentication and payment on the fan-shaped menu. When the selection of the credit card for payment is completed or the credit card for payment is automatically displayed based on a record of previous payments by the credit card, the user can make payment using such a credit card with the finger snapping. When the payment is made by the credit card, a result of the payment is displayed on the screen on the PC.

In addition, as illustrated in FIG. 14B, when the user establishes the connection to the bank website and make payment, an authentication certificate screen is displayed on the screen on the PC. When in a state where the authentication certificate screen is displayed, the user moves his/her hand on which the smart watch is worn, from left to right, the controller (not illustrated) automatically detects a bank displayed on a current screen and displays the fan-shaped menu with an authentication certificate for the detected bank ("WOORI BANK").

When the user performs the authentication with the finger snapping, the result of the authentication is displayed on the screen on the PC.

In addition, a number of a security card for the web page of the bank is automatically detected at the time of the money transfer and the money transfer is completed with the finger snapping at a time.

FIG. 14C illustrates an example in which the fan-shaped menu is displayed on the screen of the PC and thus the web browser is run.

As described above, the web browser that the user prefers is set to be on the fan-shaped menu that is used in the smart watch.

When in the logged-onto state (on the screen on the PC), the hand on which the smart watch is worn is moved from left to right, the fan-shaped menu is displayed. The user can move the hand successively rightward to place another functionality item in focus. Then, when a desired functionality item, that is, the web browser is in focus, the user performs the desired functionality item with the finger snapping.

Therefore, a customized browser that is present in the smart watch is run on the screen on the PC. Because the ID and the password for each web page are stored in the customized browser, when selecting a different website, the user can automatically log onto the different website.

FIG. 14D illustrates an example in which in a specific web browser, a connection to a different website that is not logged on is established.

When in a state where a specific web page (e.g., Daum) that is not logged on is displayed on the screen on the PC, the hand on which the smart watch is worn is waved from left to right, the controller of the smart watch checks whether the logging-on information on the specific web page is present, and when the logging-on formation is present, displays a logging-on menu with "Daum" in focus.

When the user performs the authentication with the finger snapping, the controller performs the logging-on on "Daum", and displays a user-authenticated Daum page.

FIG. 14E illustrates an example in which a messenger screen is displayed using the fan-shaped menu.

The fan-shaped menu is displayed when in a logged-on state (in a state where the wallpaper screen is displayed), the hand on which the smart watch is moved in a predetermined direction, for example, from left to right while being opened like a fan.

When the user moves his/her hand to place a functionality item, "message" in focus and then runs the functionality item, the "message" with the finger snapping, a messenger present in the smart watch is displayed on the screen on the wallpaper screen on the PC and is automatically logged on.

FIG. 14F illustrates that according to an embodiment, a program that is preset by the user to be in the smart watch is run on the screen on the PC.

The fan-shaped menu is displayed when in the logged-on state (in the state where the wallpaper screen is displayed), the hand on which the smart watch is moved from left to right while being opened like a fan. When the user moves his/her hand to place the functionality item, the "frequently-used program" in focus and then runs the functionality item, the "frequently-used program" with the finger snapping, the program that is preset by the user is displayed. If the "frequently-used program" is only one, the frequently-used program" is immediately run. If the "frequently-used program" is two or more, a fan-shaped sub-menu is displayed.

Then, when in a state where the fan-shaped sub-menu is displayed, the hand is moved from right to left while being opened, the fan-shaped menu is displayed.

In this manner, according to the present invention, the authentication is performed with the smart watch and the PC or the smartphone operating in conjunction and then the user-dedicated program or web browser that is run on the smart watch is effectively run on the screen on the PC or on the screen on the smartphone.

The screen on the PC is used as an example for the sake of description, but the present invention is not limited to the screen on the PC. The user-dedicated program or web browser that is run on the smart watch may be effectively run on the screen on the smartphone through the authentication that is performed with the smartphone and the smart watch operating in conjunction.

On the other hand, in the case of the smart watch, when the hand comes into contact with the bottom of the smart watch, the bio-information on the user, that is, the heartbeat rhythm, is measured, and thus the authentication for security is performed.

However, the present invention is not limited to the smart watch. When the user holds in his/her hand or touch on the mobile terminal or the smartphone, the bio-information on the user (for example the heartbeat rhythm and the amount of flowing blood) may be measured and then the authentication for security may be performed.

According to the present invention, a sensing unit 160 that measures the bio-information on the user to perform the authentication for security is arranged in all surfaces or one surface of the mobile terminal.

The sensing units 160 include all sensors that measure the bio-information on the user, such as a heartbeat sensor, a sensor for measuring an amount of flowing flood, and a fingerprint sensor, and may be arranged in the front surface, the rear surface, and the four lateral surfaces of the mobile terminal.

FIGS. 15A to 15B indicate positions of an input unit for performing the authentication for security in the mobile terminal.

FIG. 15A illustrates that sensors are arranged on specific portions of the mobile terminal for the authentication for security. When the specific portion is touched on or is dragged on an authentication screen for security, the bio-information is measured. The specific portion is a portion of at least one, among a front side, a rear side, an upper end, and a lower end, and a bezel. The specific portion is changed depending on a shape of the mobile terminal and on a grip type.

That is, the sensor is arranged in a portion with which a thumb comes into contact when the mobile terminal is held in the user's both hands, is arranged in a portion in which the camera is mounted, or is arranged in the lateral surface. Thus, only the holding of the mobile terminal in the hand makes it possible to measure the bio-information, thereby performing the authentication. In addition, for holding the mobile terminal in one hand, the sensor may be arranged on the front side and on the rear side.

FIG. 15B illustrates that the sensor is arranged in the entire mobile terminal for the authentication for security.

As illustrated in FIG. 15B, the sensor that measures the bio-information is positioned in the entire screen or in the entire mobile terminal. If the sensor is arranged in this manner, any portion of the mobile terminal can be pushed down or be dragged on the authentication screen for security regardless of the grip type in which the mobile terminal is held in the hand. For this reason, the sensor arrangement described above has an advantage in that the various grip types and various input methods are possible.

According to the present invention, a method of measuring the bio-information and performing the authentication for security is variously performed according to the grip type in which the mobile terminal is held and the touch type. The grip type described above indicates a one-hand grip or a both-hands grip, and the touch type indicates whether the touch is applied with the thumb or with the index finger.

FIGS. 16A and 16B illustrate a method of performing the authentication for security according to an embodiment. FIG. 16A illustrates an example in which the grip type and the authentication operation are combined and thus a specific function screen is displayed.

Generally, a portion with which a finger, such as a thumb, comes into contact differs with a size of the finger. For example, when the mobile terminal is held in a large-sized hand (for example, a father's hand), a thumb comes into contact with the screen, and when the mobile terminal is held in a small-sized hand (for example, a daughter's hand), a thumb comes into contact with the bezel.

In addition, the one-hand grip may be more convenient depending on the size of the hand. The user who feels comfortable with the one-hand grip will push down the front and rear sides of the mobile terminal at a time with the mobile terminal being held in one hand. In addition, the user may touch on the screen with the other hand holding the mobile terminal. The grip type in which the mobile terminal is held in the hand and the leftward and rightward direction of the mobile terminal may be changed. That is, when playing a game, the touch is applied with the mobile terminal being held in the both-hands grip, and when surfing the World Wide Web, the mobile terminal is held in the one-hand grip and the touch is applied.

Therefore, according to the present invention, when a grip type in which the user usually holds the mobile terminal in the hand is stored in a memory 160 and thereafter the grip type is detected, the bio-information is measured, the user is thus automatically authenticated, and then a frequently-used function screen is displayed on the display unit 151. The function screen includes a website, a game site, a bank website, a cloud image folder and the like.

For example, as illustrated in FIG. 16A, in the case of the both-hands grip in which the user touches up to the screen on the mobile terminal, the controller 180 cancels a locked state (the authentication is completed) and logs onto the game site. In the case of the both-hands grip in which the user touches up to the lateral surface of the mobile terminal, the controller 180 cancels the locked state and logs onto the cloud image folder. In addition, in the case of the one-hand grip, the bank website may be logged on according to a position of the finger on the rear surface.

FIG. 16B illustrates an example in which an operational mode is controlled according to the touched finger.

When the finger touches on the mobile terminal, according to a fingerprint of or a touched area of each finger, it is determined which finger touches on the mobile terminal.

Therefore, according to the present invention, various authentication and function screens are displayed depending not only on which grip type is used, but also on which finger touches on the mobile terminal. For example, as illustrated in FIG. 16B, when two thumbs touches on the mobile terminal in a both-hands grip state, a personal mode is activated. In addition, the thumb and an index finger touch on the mobile terminal in a one-hand grip state, an office mode is activated and when the thumb and a small finger touch on the mobile terminal, a baby mode is activated. Each mode is only one example, and the present invention is not limited to each mode. Various applications are possible with the grip type and the touch finger.

FIG. 17 is a flowchart for using the bio-information and thus performing the authentication for security when the user holding in his/her hand or touches on the mobile terminal.

According to the present invention, when in a state where the smart watch is not worn, the mobile terminal is held or touched on, the bio-information on the user (e.g., the heartbeat rhythm) is measured and the authentication is performed. When the user holds in the hand or touches on the mobile terminal, the controller 180 measures the heartbeat rhythm through a sensor within a sensing unit 140, compares the measured heartbeat rhythm with a heartbeat rhythm already stored in the memory 160, and thus performs the user authentication (S300 to S320).

According to the present invention, when the user authentication is performed in the mobile terminal, an individual security mode or a multi-security mode is activated.

The individual security mode is a mode that is activated for every user. When the user holds the mobile terminal in the hand in the individual security mode, the grip type/the bio-information (the heart rate, the amount of flowing blood, and the fingerprint) is recognized and thus a screen of the user's account and the personal information in the user are displayed.

The multi-security mode is a mode that is activated when an unidentified user holds the mobile terminal in his/her hand. When the unidentified user holds the mobile terminal in his/her hand in the multi-security mode, a guest mode is activated. In the guest mode, the unidentified user is requested to be registered as a new user. Particularly, the multi-security mode is used when the existing user hands the mobile terminal to another user and thus a new user account is added.

FIG. 18 illustrates that according to an embodiment, the user authentication is performed in the individual security mode.

Referring to FIG. 18, when in a state where the locked screen is displayed, the finger comes into contact with the screen on the mobile terminal (the smartphone or a tablet PC) the sensor within the sensing unit 160 measures the user's heartbeat rhythm, and the controller 180 compares the measured heartbeat rhythm with the already-registered heartbeat rhythm and thus authenticates the user. Thereafter, the controller 180 automatically cancels the locked screen.

FIG. 19 illustrates that according to another embodiment, the user authentication is performed in the individual security mode.

If a gallery, a message, or the like is touched on when it is locked, the user authentication is automatically performed and the locked state is canceled. At this time, if the user of the authenticated mobile terminal holds the mobile terminal in his/her hand, the cloud folder and a hidden folder are displayed together. However, if another person holds the mobile terminal in his/her hand, the cloud folder and the hidden folder are not displayed.

FIGS. 20A and 20B illustrate that according to an embodiment, the user authentication is performed in the multi-security mode.

According to the present invention, an unidentified (unauthenticated) user B uses the mobile terminal that was used by a user A, the controller 180 performs switching to the guest mode. In the guest mode, hidden content is not displayed, the user automatically logs off the previous website or application, and account information for the previous website and application is no longer displayed.

As illustrated in FIG. 20A, in the guest mode, the user B can register a new account. When the user B arbitrarily registers his/her own account, only a name of the user B is displayed on an empty screen. When the user A performs the authentication in this state, a registration screen is displayed into which detailed information on the user B is input. Therefore, the user B can input the detailed information into the registration screen and thus can register a new account.

FIG. 20B illustrates an example in which the account is registered when the user A uses the mobile terminal, the user B then uses the mobile terminal in the guest mode, and the user A then uses the mobile terminal back. That is, when the user A uses the mobile terminal (in the individual security mode) and then hands the mobile terminal to the user B whose account is temporarily registered, the user B can limitedly use content in the guest mode.

Thereafter, if the user A uses the mobile terminal back, the controller 180 outputs a message asking whether or not an account of the user B will be registered. Therefore, if the user determines to register the account of the user B, the controller 180 performs a registration process based on the information on the user B that is input.

FIG. 21 illustrates a method in which at the time of double locking, the authentication is performed.

As discussed above, the user authentication is first performed with the heartbeat rhythm and thus the hidden folder is displayed on the screen. If the hidden folder is preset to be in the locked state, the locked state is canceled by a separate touch operation.

For example, when the user who is first authenticated applies a multi-touch (two touches) to the locked folder, the locked state is canceled, and when an unauthenticated user applies the multi-touch (two touches) to the locked folder, the locked state is not canceled.

FIGS. 22A and 22B are examples in which the authentication of an application on the mobile terminal is performed in the smart watch.

When the smart watch approaches the mobile terminal, the smart watch is connected to the mobile terminal through the short-distance communication (BT or NFC). Therefore, as illustrated in FIG. 22A, when the user touches on a locked application with his/her hand on which the smart watch is worn, the controller of the smart watch measures the user's heartbeat rhythm and thus automatically performs the authentication operation. At this time, a message indicating that an authentication process is in progress is displayed on the screen on the smart watch, along with the "name of the application" that is touched on.

Thereafter, when the user authentication is completed, the locked state of the application that is displayed on the screen on the mobile terminal is canceled and thus the application is automatically run.

In addition, as illustrated in FIG. 22B, if the user presets a photo folder to be in the locked state, the moment the photo folder is touched on, the authentication is performed on the wearer in the smart watch to verify whether or not he/she is a registered user. When the authentication is completed, the locked state of the photo folder is canceled and thus the photo folder is opened. Also in this case, the message indicating that the authentication process is in progress is displayed on the screen on the smart watch, along with a "name of the folder" that is touched on.

FIG. 23 illustrates an example in which automatic authentication and payment are performed at the time of Internet shopping.

According to the present invention, purchasing of an application (App) (for example, Android App or iOS App) or the automatic authentication and payment at the time of the Internet shopping is performed using the bio-information.

As illustrated in FIG. 23, when the user applies the multi-touch (two-touch clicks) to an application that he/she wants to purchase on an Internet shopping mall screen, the controller 180 of the mobile terminal performs the user authentication using the user's heartbeat rhythm, refers to the previous payment history, and thus immediately automatically displays a payment screen for paying for the application by a predetermined credit card.

The present invention is not limited to this. According to the present invention, the automatic authentication and payment may be performed in the smart watch.

FIGS. 24A to 24C illustrate that according to an embodiment, the personal information is automatically input using the bio-information.

According to the present invention, when with two fingers (two touches), the user pushes down a specific region of a screen for inputting a password of the authentication certificate and the personal information, the controller 180 authenticates the user using the bio-information (e.g., the heartbeat rhythm) and then enables the user's password of the authentication certificate or the personal information to be automatically input into the specific region. This removes inconvenience of separately inputting the password of the authentication certificate or the OTP (FIGS. 24A and 24B).

In addition, as illustrated in FIG. 24C, when the user applies the multi-touch to a window for inputting the ID or the password at the time of logging onto the web page, the controller 180 enables the user's ID and password to be automatically input, and thus performs the logging-on. When the logging-on is completed, the controller 180 displays a web page that the user usually visits frequently.

As described above, the present invention can perform a interworking function (e.g., the user registration/authentication between the smart watch and the mobile terminal by using the biometrics technology to the smart watch, and can conveniently control operations of the mobile terminal using the smart watch.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller of the mobile terminal.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

The invention claimed is:

1. A smart watch comprising:
a display unit;
a sensor mounted in a bottom of a smart watch; and
a controller configured to:
measure a heartbeat rhythm using the sensor when an authentication request signal for an application displayed on an external apparatus is detected, wherein the external apparatus is interworked with the smart watch,
perform an authentication for the application by comparing the measured heartbeat rhythm with a stored heartbeat rhythm, and
transmit a result of the authentication to the external apparatus so that the external apparatus can execute the application,
wherein the external apparatus is further configured to:
detect a grip type in which a user holds a mobile terminal in one hand or both hands,
automatically measure the heartbeat rhythm using the sensor when a stored specific grip type is detected,
perform a user authentication by comparing the measured heartbeat rhythm with a stored heartbeat rhythm, and
display a function screen that is frequently used in the detected specific grip type when the authentication is completed,
wherein the function screen includes at least one a website, a game site, a bank website, and a cloud image folder, and
wherein the controller is further configured to:
execute a different operational mode according to the detected specific grip type and which finger touches on the mobile terminal.

2. The smart watch of claim 1, wherein the authentication request signal is input into the smart watch or is received from the external apparatus.

3. The smart watch of claim 1, wherein the authentication request signal is generated when user authentication is selected from an authentication screen, and
wherein the authentication screen is a screen for inputting a personal information of a user, and includes a payment screen of an on-line banking site or an on-line shopping mall, a web page, a logging-on screen of an application or a messenger and a locked screen.

4. The smart watch of claim 3, wherein the personal information includes at least one among an authentication certificate, a password, a credit card number, an account number, and ID.

5. The smart watch of claim 1, wherein the controller displays the result of the authentication on a screen of the smart watch,
wherein the external apparatus transmits the authentication request signal, along with information necessary for the authentication, and
wherein the information necessary for the authentication includes payment information or money transfer information.

6. The smart watch of claim 1, wherein the external apparatus controls operation of the application according to a gesture that is made using a user's hand on which the smart watch is worn.

7. The smart watch of claim 6, wherein the external apparatus displays a fan-shaped menu for functionality items that can be performed between the smart watch and the external apparatus when the user's hand on which the smart watch is worn is moved in a predetermined direction while being opened.

8. The smart watch of claim 7, wherein the fan-shaped menu is displayed on a wallpaper screen or a predetermined website, and includes functionality items including authentication and payment, a web browser, a messenger, and a frequently-used program.

9. The smart watch of claim 7, wherein a functionality item associated with the application is in focus on the fan-shaped menu.

10. The smart watch of claim 6, wherein the external apparatus includes at least one or more sensors that senses the heartbeat rhythm, and
wherein the sensors are positioned in a specific portion, through the screen or through the external apparatus.

11. The smart watch of claim 10, wherein the specific portion includes at least one, among a front side, a rear side, an upper end, and a lower end, and a bezel of the external apparatus, and is changed depending on a shape of the external apparatus and on a grip type.

* * * * *